United States Patent
Kim et al.

(10) Patent No.: US 9,993,221 B2
(45) Date of Patent: Jun. 12, 2018

(54) X-RAY APPARATUS AND SYSTEM

(71) Applicant: SAMSUNG ELECTRONICS CO., LTD., Suwon-si (KR)

(72) Inventors: Seung-hoon Kim, Suwon-si (KR); Sang-woo Kim, Seoul (KR); Jung-woo Kim, Suwon-si (KR); Sung-jin Park, Suwon-si (KR); Ja-woong Yoon, Seoul (KR); Eun-aeh Cho, Suwon-si (KR); Jin-beom Hong, Seoul (KR); Do-hyeong Hwang, Gunpo-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 111 days.

(21) Appl. No.: 14/945,916

(22) Filed: Nov. 19, 2015

(65) Prior Publication Data

US 2016/0135779 A1    May 19, 2016

Related U.S. Application Data

(60) Provisional application No. 62/081,745, filed on Nov. 19, 2014.

(30) Foreign Application Priority Data

Feb. 25, 2015 (KR) ........................ 10-2015-0026751
Jul. 7, 2015 (KR) ........................ 10-2015-0096782

(51) Int. Cl.
*A61B 6/08* (2006.01)
*A61B 6/00* (2006.01)
*A61B 6/06* (2006.01)

(52) U.S. Cl.
CPC ................ *A61B 6/547* (2013.01); *A61B 6/06* (2013.01); *A61B 6/4405* (2013.01)

(58) Field of Classification Search
CPC ........... A61B 6/587; A61B 6/08; A61B 6/547; A61B 6/4405; A61B 6/4441; A61B 6/588;
(Continued)

(56) References Cited

U.S. PATENT DOCUMENTS 4,641,330 A    2/1987   Herwig et al.
5,693,948 A   12/1997   Sayed et al.
(Continued)

FOREIGN PATENT DOCUMENTS

JP          6-327665 A    11/1994
JP    2001-0120525 A    5/2001
(Continued)

OTHER PUBLICATIONS

ENERGY STAR, "ENERGY STAR® Program Requirements Product Specification for Medical Imaging Equipment", Preliminary Test Method for Determining Medical Imaging Equipment Energy Use, Rev. Jan. 2014, total 6 pages.

*Primary Examiner* — Hoon Song
(74) *Attorney, Agent, or Firm* — Sughrue Mion, PLLC

(57) ABSTRACT

An X-ray apparatus includes an X-ray radiator configured to radiate an X-ray, and a controller acquiring orientation information of the X-ray radiator and orientation information of at least one X-ray detector, selecting the at least one X-ray detector based on the orientation information of the X-ray radiator and the orientation information of the at least one X-ray detector, and determining a power mode of the selected X-ray detector to be a power consumption mode and a power mode of an X-ray detector that is not selected, to be a power save mode.

20 Claims, 38 Drawing Sheets

(58) Field of Classification Search
CPC ........... A61B 6/04; A61B 6/467; A61B 90/39;
A61B 6/0492; A61B 6/461; A61B 6/035;
A61N 2005/1061
See application file for complete search history.

(56) References Cited

U.S. PATENT DOCUMENTS

| | | |
|---|---|---|
| 5,773,832 A | 6/1998 | Sayed et al. |
| 5,835,083 A | 11/1998 | Nielsen et al. |
| 5,867,561 A | 2/1999 | Strasser et al. |
| 6,282,263 B1 | 8/2001 | Arndt et al. |
| 7,050,539 B2 | 5/2006 | Loef et al. |
| 7,514,703 B2 | 4/2009 | Iwakiri |
| 7,852,986 B2 | 12/2010 | Loef et al. |
| 8,325,037 B2 | 12/2012 | Luemkemann et al. |
| 8,637,829 B2 | 1/2014 | Mazuir et al. |
| 2012/0033783 A1 | 2/2012 | Katayama |
| 2013/0038738 A1* | 2/2013 | Ando ................... A61B 6/4266 348/162 |
| 2013/0136240 A1 | 5/2013 | Causape Rodriguez et al. |
| 2013/0259189 A1 | 10/2013 | Sakai |
| 2013/0311807 A1 | 11/2013 | Woo et al. |
| 2015/0312999 A1 | 10/2015 | Takahashi et al. |

FOREIGN PATENT DOCUMENTS

| | | |
|---|---|---|
| JP | 2002-0224095 A | 8/2002 |
| JP | 2005-0319337 A | 11/2005 |
| JP | 2010-0046315 A | 3/2010 |
| JP | 2011-0248158 A | 12/2011 |
| JP | 2014-0132933 A | 7/2014 |
| KR | 10-0706224 B1 | 4/2007 |
| KR | 10-0758989 B1 | 9/2007 |
| KR | 10-1097058 B1 | 12/2011 |
| KR | 10-1349406 B1 | 1/2014 |

* cited by examiner

X-RAY APPARATUS AND SYSTEM

RELATED APPLICATIONS

This application claims the benefit of Provisional U.S. Patent Application No. 62/081,745, filed on Nov. 19, 2014, in the U.S. Patent and Trademark Office, and priority from Korean Patent Application No. 10-2015-0026751, filed on Feb. 25, 2015, and Korean Patent Application No. 10-2015-0096782, filed on Jul. 7, 2015, in the Korean Intellectual Property Office, the disclosures of which are incorporated herein in their entireties by reference.

BACKGROUND

1. Field

Apparatuses and methods consistent with the exemplary embodiments relate to an X-ray apparatus and system, and more particularly, to an X-ray apparatus and system which may reduce power consumption.

2. Description of the Related Art

In general, an X-ray is an electromagnetic wave having a wavelength of 0.01~100 Å and having a property of being transmittable through an object so that it may be widely used in medical equipment for capturing the interior of a living body or in non-destructive testing equipment used in various industrial fields.

An X-ray apparatus using an X-ray may transmit an X-ray from an X-ray source through an object and detect a difference in the strength of the transmitted X-ray by using an X-ray detector, thereby obtaining an X-ray image of the object. The X-ray image may be used to analyze the internal structure of the object and diagnose the object. The X-ray apparatus facilitates easy analysis of the internal structure of an object by using a principle that transmittance of an X-ray varies according to the density of the object and the atomic number of an atom forming the object. When the wavelength of an X-ray is reduced, transmittance may be increased and a screen may become brighter.

SUMMARY

One or more embodiments of the exemplary embodiments include an X-ray apparatus and system which may reduce power consumption.

Additional aspects will be set forth in part in the description which follows and, in part, will be apparent from the description, or may be learned by practice of the presented embodiments.

According to one or more exemplary embodiments, an X-ray apparatus includes an X-ray radiator configured to radiate an X-ray, and a controller configured to acquire orientation information of the X-ray radiator and orientation information of a plurality of X-ray detectors, select an X-ray detector of the plurality of X-ray detectors based on the orientation information of the X-ray radiator and the orientation information of the plurality of X-ray detectors, and set a power mode of the selected X-ray detector to be a power consumption mode and a power mode of an unselected X-ray detector of the plurality of X-ray detectors to be a power save mode.

When at least one X-ray detector of the plurality of X-ray detectors is coupled to a receptor, the controller may determine a power mode of the receptor to be the same as the power mode of the X-ray detector that is coupled to the receptor.

The orientation information of the plurality of X-ray detectors may include information indicating whether each of the plurality of X-ray detectors is coupled to the receptor.

The controller may acquire the orientation information of the X-ray radiator based on a positioning mode of the X-ray apparatus, one of a stand mode, a table mode, and a portable mode.

The X-ray apparatus may further include an input unit that receives a user's input for selecting the positioning mode.

When a non-usage time of the X-ray apparatus exceeds a threshold time, the controller may switch an operation mode of the X-ray apparatus to a sleep mode and adaptively sets the threshold time.

The controller may acquire a usage time distribution function that is a frequency of using the X-ray apparatus with respect to a time interval between scanning operations performed by the X-ray apparatus, acquire a utility function based on the usage time distribution function, and set a time to maximize the utility function as the threshold time.

The controller may update the usage time distribution function, the utility function, and the threshold time.

The X-ray apparatus may further include a collimator that includes a blade for blocking the X-ray and a blade driver for moving the blade, wherein the controller controls the blade driver to move the blade to a first reference position and obtains a first relative position of the blade moved from the first reference position until the operation mode is switched to the sleep mode.

When the operation mode is switched to the sleep mode and then to a use mode, the controller may control the blade driver to move the blade to the first reference position and control the blade driver to move the blade by the first relative position from the first reference position.

The X-ray apparatus may further include a plurality of filters for filtering the X-ray and a filter driver for moving the plurality of filters, wherein the controller controls the filter driver to move the plurality of filters to second reference positions and obtains second relative positions of the plurality of filters moved from the second reference positions until the operation mode is switched to the sleep mode, and when the operation mode is switched to the sleep mode and then to a use mode, the controller controls the filter driver to move the plurality of filters to the second reference positions and controls the filter driver to move the plurality of filters by the second relative positions from the second reference position.

The X-ray apparatus may further include a mode indicator that indicates that the operation mode of the X-ray apparatus is the sleep mode.

The mode indicator may include a light-emitting element and, when the operation mode of the X-ray apparatus is the sleep mode, the light-emitting element may flicker at a speed equal to or less than a predetermined speed.

According to one or more exemplary embodiments, a workstation includes a communicator configured to receive orientation information of an X-ray radiator comprised in an X-ray apparatus and orientation information of a plurality of X-ray detectors; and a controller configured to select an X-ray detector of the plurality of X-ray detectors based on the orientation information of the X-ray radiator and the orientation information of the plurality of X-ray detectors, and set a power mode of the selected X-ray detector to be a power consumption mode and a power mode of an unselected X-ray detector of the plurality of X-ray detectors to be a power save mode.

When at least one X-ray detector of the plurality of X-ray detectors is coupled to a receptor, the controller may determine a power mode of the receptor to be the same as the power mode of the X-ray detector that is coupled to the receptor.

The orientation information of the plurality of X-ray detectors may include information indicating whether each of the plurality of X-ray detectors is coupled to the receptor.

The controller may acquire the orientation information of the X-ray radiator based on a positioning mode of the X-ray apparatus, one of a stand mode, a table mode, and a portable mode.

The workstation may further include an input unit that receives a user's input for selecting the positioning mode.

When non-usage times of the X-ray apparatus and the workstation exceed a threshold time, the controller may switch an operation mode of the X-ray apparatus and the workstation to a sleep mode and adaptively sets the threshold time.

The controller may acquire a usage time distribution function that is a frequency of using the X-ray apparatus with respect to a time interval between scanning operations performed by the X-ray apparatus, acquire a utility function based on the usage time distribution function, and set a time to maximize the utility function as the threshold time.

The controller may update the usage time distribution function, the utility function, and the threshold time.

The X-ray apparatus may further include a collimator that comprises a blade for blocking the X-ray and a blade driver for moving the blade. The controller may control the blade driver to move the blade to a first reference position and obtains a first relative position of the blade moved from the first reference position until the operation mode is switched to the sleep mode.

When the operation mode is switched to the sleep mode and then to a use mode, the controller may control the blade driver to move the blade to the first reference position and control the blade driver to move the blade by the first relative position from the first reference position.

The X-ray apparatus may further include a plurality of filters for filtering the X-ray and a filter driver for moving the plurality of filters. The controller may control the filter driver to move the plurality of filters to second reference positions and obtains second relative positions of the plurality of filters moved from the second reference positions until the operation mode is switched to the sleep mode. When the operation mode is switched to the sleep mode and then to a use mode, the controller may control the filter driver to move the plurality of filters to the second reference positions and control the filter driver to move the plurality of filters by the second relative positions from the second reference position.

According to one or more exemplary embodiments, a method of operating an X-ray system includes acquiring orientation information of an X-ray radiator and orientation information of at least one X-ray detector of a plurality of X-ray detectors; selecting an X-ray detector of the plurality of X-ray detectors based on the orientation information of the X-ray radiator and the orientation information of the at least one X-ray detector; and setting a power mode of the selected X-ray detector to be a power consumption mode and a power mode of an unselected X-ray detector of the plurality of X-ray detectors to be a power save mode.

According to one or more exemplary embodiments, there is provided a non-transitory computer readable storage medium having stored thereon a program, which when executed by a computer, performs the above method.

According to one or more exemplary embodiments, an X-ray apparatus includes a collimator comprising a blade for blocking an X-ray and a blade driver for moving the blade, and a controller controlling the blade driver to move the blade to a reference position and obtaining a relative position of the blade moved from the reference position.

When power supplied to the collimator is interrupted and then resupplied after the controller obtains the relative position, the controller may control the blade driver to move the blade to the reference position and controls the blade driver to move the blade by the relative position from the reference position.

When an operation mode is switched to a sleep mode and then to a user mode after the controller obtains the relative position, the controller may control the blade driver to move the blade to the reference position and control the blade driver to move the blade by the relative position from the reference position.

The collimator may further include a sensor sensing that the blade is located at the reference position and transmitting a signal indicating that the blade is located at the reference position to the controller.

The controller may obtain the relative position of the blade moved from the reference position based on power supplied to the blade driver after the blade is moved to the reference position.

The X-ray apparatus may further include a plurality of filters for filtering the X-ray and a filter driver for moving the plurality of filters. The controller may control the filter driver to move the plurality of filters to second reference positions and obtain second relative positions of the plurality of filters moved from the second reference positions.

When power supplied to the filter driver is interrupted and then resupplied after the controller obtains the second relative positions, the controller may control the filter driver to move the plurality of filters to the second reference positions and control the filter driver to move the plurality of filters by the second relative positions from the second reference positions.

When an operation mode is switched to a sleep mode and then to a user mode after the controller obtains the second relative positions, the controller may control the filter driver to move the plurality of filters to the second reference positions and control the filter driver to move the plurality of filters by the second relative positions from the second reference positions.

According to one or more exemplary embodiments, an X-ray apparatus includes a plurality of filters for blocking an X-ray, a filter driver for moving the blade, and a controller controlling the filter driver to move the plurality of filters to reference positions and obtaining relative positions of the plurality of filters moved from the reference positions.

When power supplied to the filter driver is interrupted and then resupplied after the controller obtains the relative positions, the controller may control the filter driver to move the plurality of filters to the reference positions and control the filter driver to move the plurality of filters by the relative positions from the reference positions.

According to one or more exemplary embodiments, a workstation includes a communicator configured to perform communication with an X-ray apparatus, the X-ray apparatus including a collimator that comprises a blade for blocking an X-ray and a blade driver for moving the blade, and a controller controlling the blade driver to move the blade to a reference position and obtaining a relative position of the blade moved from the reference position.

When power supplied to the X-ray apparatus is interrupted and then resupplied after the controller obtains the relative position, the controller may control the blade driver to move the blade to the reference position and control the blade driver to move the blade by the relative position from the reference position.

The X-ray apparatus may further include a plurality of filters for filtering the X-ray and a filter driver for moving the plurality of filters. The controller may control the filter driver to move the plurality of filters to second reference positions and obtain second relative positions of the plurality of filters moved from the second reference positions. When power supplied to the X-ray apparatus is interrupted and then resupplied, the controller may control the filter driver to move the plurality of filters to the second reference positions and control the filter driver to move the plurality of filters by the second relative positions from the second reference positions.

According to one or more exemplary embodiments, a method of operating an X-ray system includes controlling a blade driver to move a blade for blocking an X-ray to a reference position, obtaining a relative position of the blade moved from the reference position, when power is interrupted and then resupplied, controlling the blade driver to move the blade back to the reference position, and controlling the blade driver to move the blade by the relative position from the reference position.

According to one or more exemplary embodiments, a method of operating an X-ray system includes controlling a filter driver to move a plurality of filters for blocking an X-ray to reference positions, obtaining relative positions of the plurality of filters moved from the reference positions, when power is interrupted and then resupplied, controlling the filter driver to move the plurality of filters back to the reference positions, and controlling the filter driver to move the plurality of filters by the relative positions from the reference positions.

According to one or more exemplary embodiments, there is provided a non-transitory computer readable storage medium having stored thereon a program, which when executed by a computer, performs one of the above methods.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
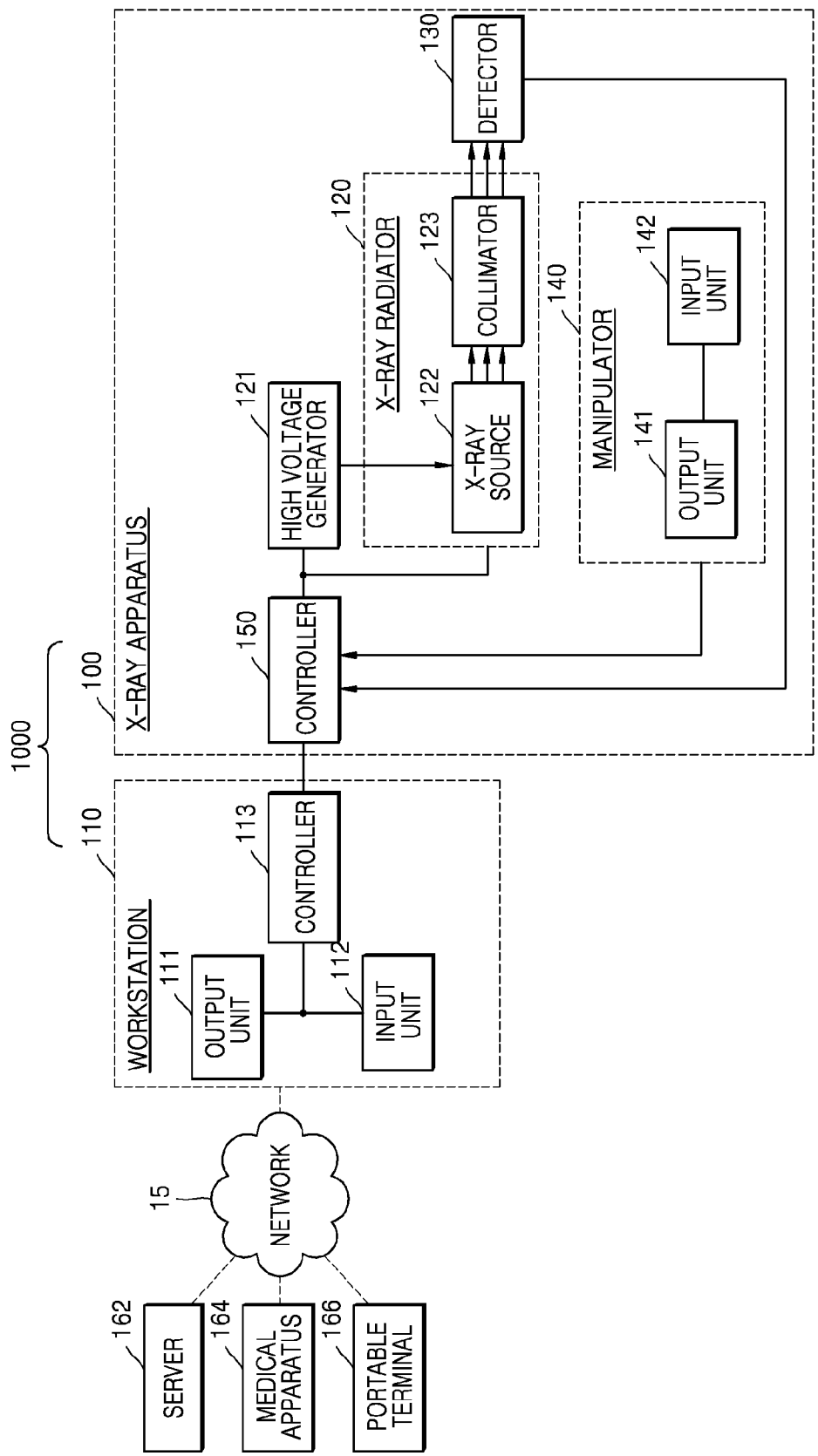
FIG. 1 is a block diagram illustrating a structure of an X-ray system.

The attached drawings for illustrating exemplary embodiments of the present disclosure are referred to in order to gain a sufficient understanding of the present disclosure, the merits thereof, and the objectives accomplished by the implementation of the present disclosure. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the exemplary embodiments, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the present disclosure.

Throughout the specification, an "image" may denote multi-dimensional data composed of discrete image elements (for example, pixels in a two-dimensional image and voxels in a three-dimensional image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, abdomen photographing, skeleton photographing, nasal sinuses photographing, neck soft tissue photographing, and breast photographing.

FIG. 1 is a block diagram of an X-ray system 1000.

Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region irradiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10V and a current of about 3 to 5 A may be applied to an electric wire connected to the filament to heat the filament.

In addition, when a high voltage of about 10 to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is disposed opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, energy of the X-ray (energy of photons) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include a manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray photographing. The controller 150 may control or manipulate the X-ray apparatus 100 according to the information received by the input unit 142. The output unit 141 may output sound representing information related to a photographing operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 200. The controller 113 may control the workstation 110 and the X-ray apparatus 200.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. In some exemplary embodiments, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, exemplary embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed in two steps.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to photographing in addition to the X-ray radiation. In FIG. 1, the output unit 141 is included in the manipulator 140; however, the exemplary embodiments are not limited thereto, and the output unit 141 or a portion of the output unit 141 may be located elsewhere. For example, the output unit 141 may be located on a wall of an examination room in which the X-ray photographing of the object is performed.

The controllers 113 and 150 control locations of the X-ray radiator 120 and the detector 130, photographing timing, and photographing conditions, according to photographing conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the control units 113 and 150 adjust the location of the detector 130 according to a predetermined photographing condition, and control operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
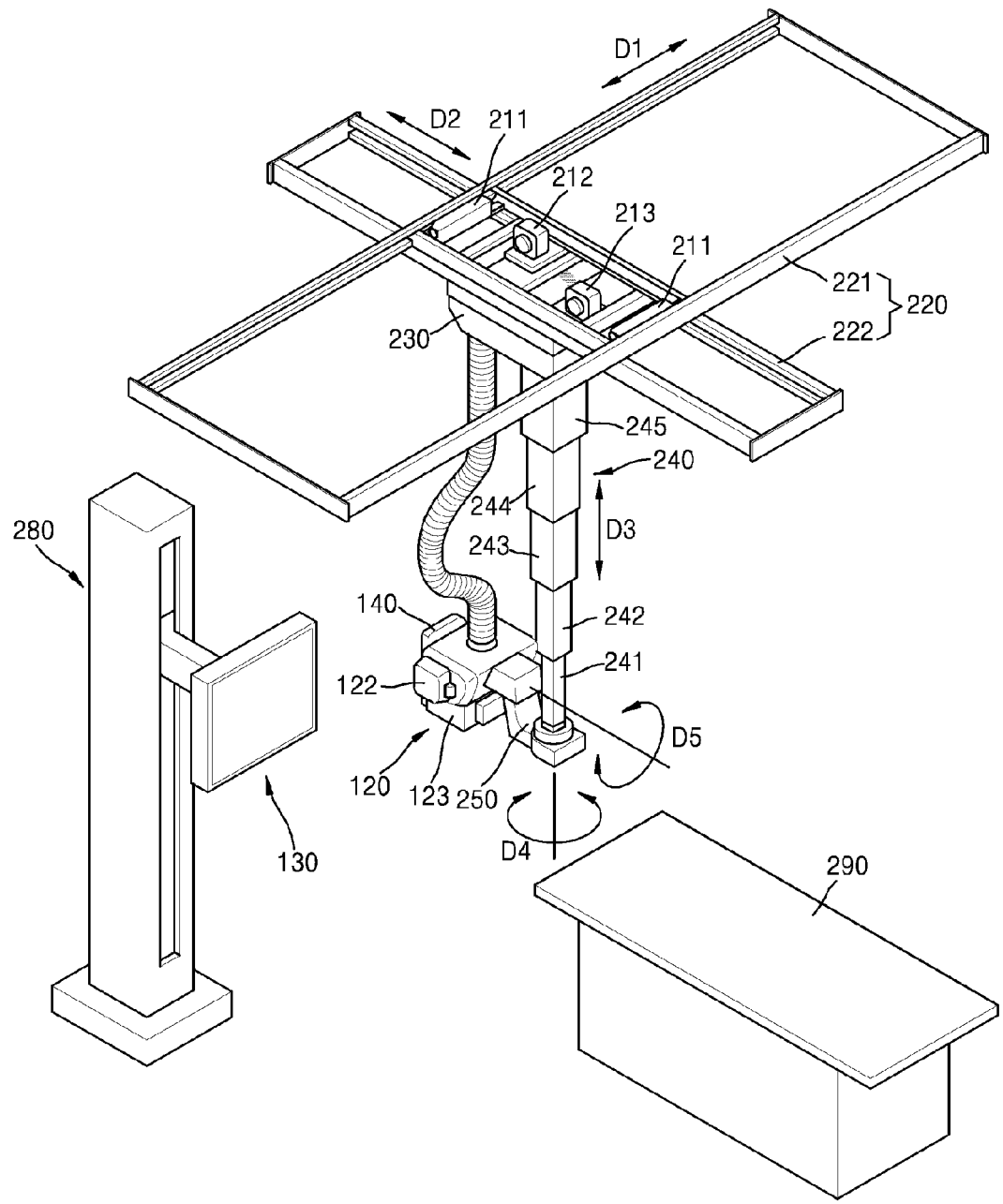
FIG. 2 is a perspective view of a fixed-type X-ray apparatus.

FIG. 2 is a perspective view of a fixed type X-ray apparatus 200. The fixed type X-ray apparatus 200 may be an exemplary embodiment of the X-ray apparatus 100 of FIG. 1. Components included in the fixed type X-ray apparatus 200 that are the same as those of the X-ray apparatus 100 of FIG. 1 use the same reference numerals, and repeated descriptions thereof will be omitted.

Referring to FIG. 2, the fixed type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the X-ray apparatus 200 is disposed.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is disposed under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table type receptor 290 or a stand type receptor 280.

A rotating joint 250 is disposed between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be disposed at various locations in consideration of design convenience. For example, the first motor 211, moving the second guide rail 222 in the first direction D1, may be disposed around the first guide rail 221, the second motor 212, moving the moving carriage 230 in the second direction D2, may be disposed around the second guide rail 222, and the third motor 213, increasing or reducing the length of the post frame 240 in the third direction D3, may be disposed in the moving carriage 230. In another example, the first, second, and third motors 211, 212, and 213 may be connected to a driving power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be disposed between the rotating joint 250 and the post frame 240 and between the rotating joint 250 and the X-ray radiator 120 in order to rotate the X-ray radiator 120 in the fourth and fifth directions D4 and D5.

The manipulator 140 may be disposed on a side surface of the X-ray radiator 120.

Although FIG. 2 shows the fixed type X-ray apparatus 200 connected to the ceiling of the examination room, the fixed type X-ray apparatus 200 is merely an example for convenience of comprehension. That is, X-ray apparatuses according to exemplary embodiments of the present disclosure may include X-ray apparatuses having various structures that are well known to one of ordinary skill in the art, for example, a C-arm-type X-ray apparatus and an angiography X-ray apparatus, in addition to the fixed type X-ray apparatus 200 of FIG. 2.

Figure 3:
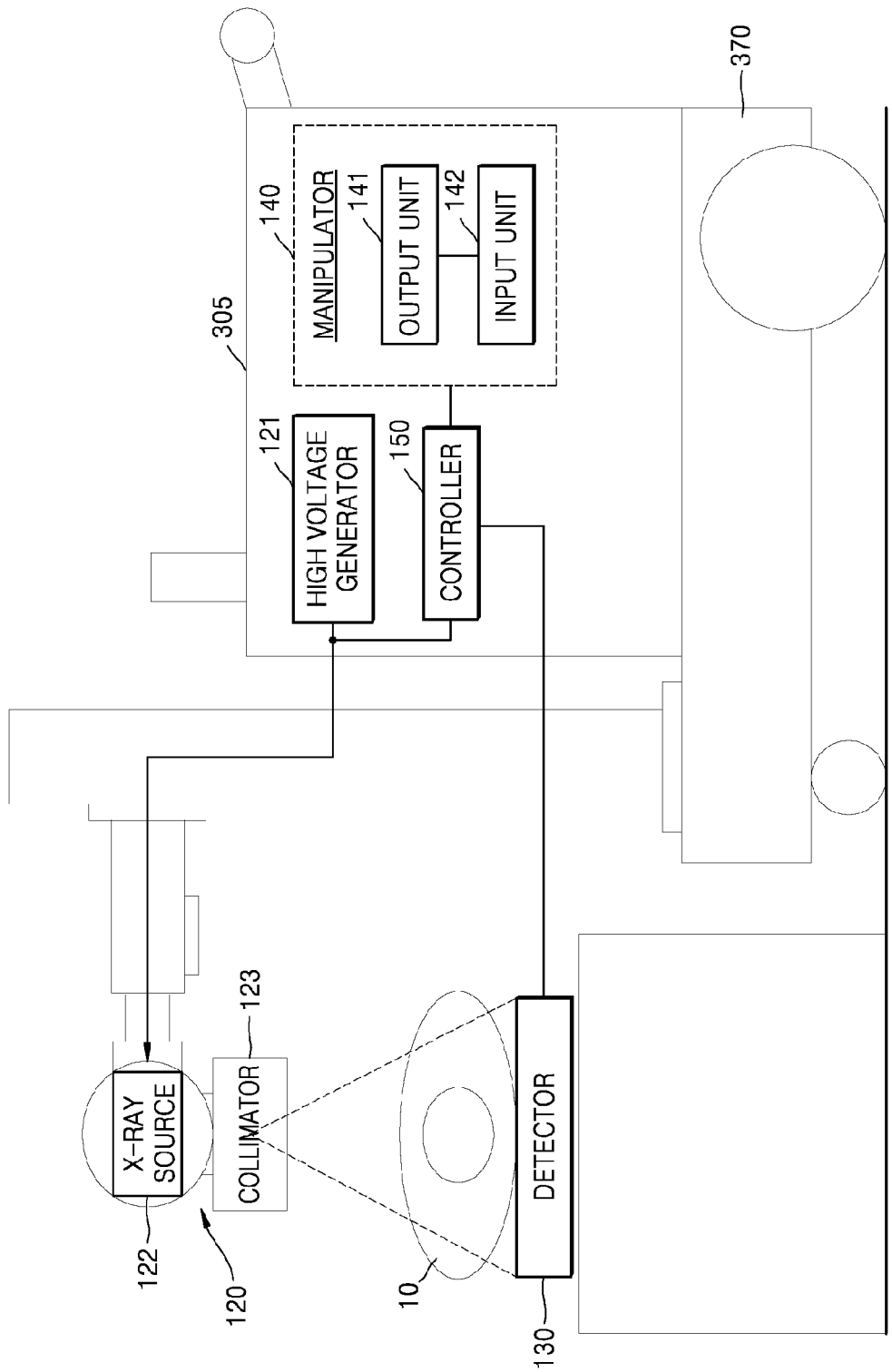
FIG. 3 is a block diagram of a mobile X-ray apparatus.

FIG. 3 is a diagram showing a configuration of a mobile X-ray apparatus 300 capable of performing an X-ray photographing operation regardless of a place where the photographing operation is performed. The mobile X-ray apparatus 300 may be an exemplary embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and a repeated description thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object 10 and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region irradiated by the X-ray.

The detector 130 in FIG. 3 may not be combined with any receptor, and the detector 130 may be a portable detector which can exist anywhere.

In FIG. 3, the manipulator 140 is included in the main unit 305; however, exemplary embodiments are not limited thereto. For example, as illustrated in FIG. 2, the manipulator 140 of the mobile X-ray apparatus 300 may be disposed on a side surface of the X-ray radiator 120.

Figure 4:
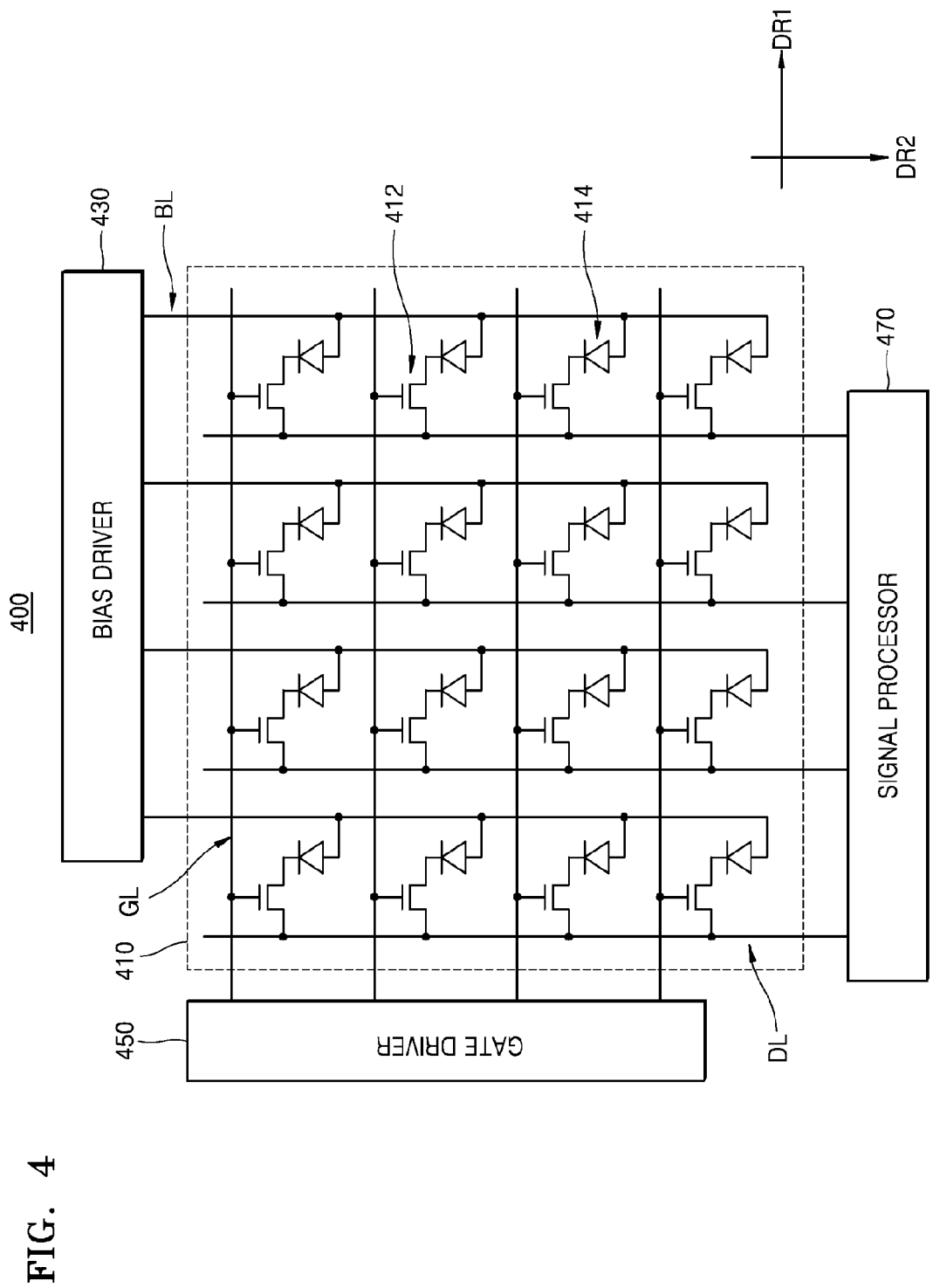
FIG. 4 illustrates a detailed structure of a detector.

FIG. 4 is a schematic diagram showing a detailed configuration of a detector 400. The detector 400 may be an exemplary embodiment of the detector 130 of FIGS. 1-3. The detector 400 may be an indirect type detector.

Referring to FIG. 4, the detector 400 may include a scintillator (not shown), a photodetecting substrate 410, a bias driver 430, a gate driver 450, and a signal processor 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. FIG. 4 shows four bias lines BL formed along the second direction DR2 as an example.

The bias driver 430 is electrically connected to the bias lines BL so as to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 so as to apply a reverse bias voltage to the photodiodes 414. On the other hand, the bias driver 430 may apply a voltage that is greater than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data. The signal processor 470 may output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit.

Figure 5:
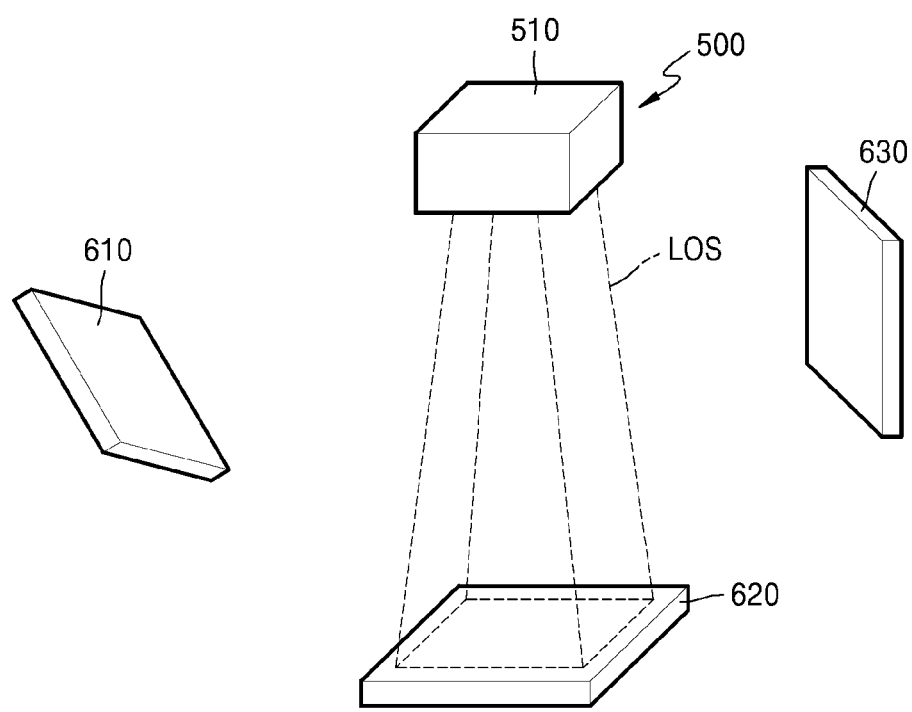
FIG. 5 illustrates an example of an operation of an X-ray apparatus according to an exemplary embodiment.

FIG. 5 illustrates an example of an operation of an X-ray apparatus 500 according to an exemplary embodiment.

Referring to FIG. 5, the X-ray apparatus 500 may include an X-ray radiator 510. The X-ray radiator 510 may be configured to radiate an X-ray. The X-ray radiator 510 has a structure corresponding to that of the X-ray radiator 120 of FIGS. 1 to 3 and the above descriptions of the X-ray radiator 120 may be applied to the X-ray radiator 510. Although, for convenience of explanation, FIG. 5 illustrates only the X-ray radiator 510 as an element included in the X-ray apparatus 500, the X-ray apparatus 500 may further include other elements.

At least one X-ray detector 610, 620, or 630 may be disposed around the X-ray apparatus 500. Although FIG. 5 illustrates that the at least one X-ray detector 610, 620, or 630 is provided separate from the X-ray apparatus 500, any one X-ray detector 610, 620, or 630 may be included in the X-ray apparatus 500. Although FIG. 5 illustrates the three X-ray detectors, the first X-ray detector 610, the second X-ray detector 620, and the third X-ray detector 630, FIG. 5 does not limit the number of X-ray detectors which may be disposed around the X-ray apparatus 500. For example, only one X-ray detector may be disposed around the X-ray apparatus 500. Even if the following figures show a plurality of X-ray detectors disposed around an X-ray apparatus, it is noted that this does not preclude a case where only one X-ray detector is disposed around the X-ray apparatus. That is, at least one X-ray detector may be disposed around an X-ray apparatus.

The X-ray apparatus 500 may acquire orientation information of the X-ray radiator 510 and orientation information of the at least one X-ray detector 610, 620, or 630.

The orientation information of the X-ray radiator 510 may include at least one of positional information and directional information of the X-ray radiator 510. The orientation information of each of the at least one X-ray detector 610, 620, or 630 may include at least one of the positional information and directional information of each of the at least one X-ray detector 610, 620, or 630. The positional information of an element such as the X-ray radiator 510 and the at least one X-ray detector 610, 620, or 630 denotes the position of the element, and the directional information of the element denotes a direction that the element faces.

The X-ray apparatus 500 may select the at least one X-ray detector 610, 620, or 630, based on the orientation information of the X-ray radiator 510 and the orientation information of the at least one X-ray detector 610, 620, or 630. The X-ray apparatus 500 may select the second X-ray detector 620 that faces the X-ray radiator 510.

According to the present exemplary embodiment, the orientation information of the X-ray radiator 510 may include information indicating a line of sight (LOS) that is a line according to an X-ray radiation direction of the X-ray radiator 510. The X-ray apparatus 500 may select the second X-ray detector 620 that meets the LOS of the X-ray radiator 510, based on the orientation information of the at least one X-ray detector 610, 620, or 630. In other words, when the LOS of the X-ray radiator 510 lies on the second X-ray detector 620, the X-ray apparatus 500 may select the second X-ray detector 620.

The X-ray apparatus 500 may determine a power mode, e.g., set a power mode, of the second X-ray detector 620 that is selected, to be a power consumption mode. The X-ray apparatus 500 may determine, e.g., set a power mode, the power modes of the first X-ray detector 610 and the third X-ray detector 630 that are not selected X-ray detectors, to be a power save mode.

The at least one X-ray detector 610, 620, or 630 may receive power from the X-ray apparatus 500 or receive power separate from the X-ray apparatus 500. For example, when the at least one X-ray detector 610, 620, or 630 is coupled to the X-ray apparatus 500, the at least one X-ray detector 610, 620, or 630 may receive power from the X-ray apparatus 500. When the at least one X-ray detector 610, 620, or 630 is a portable X-ray detector, the at least one X-ray detector 610, 620, or 630 may receive power through batteries included in the at least one X-ray detector 610, 620, or 630, which are separated from the X-ray apparatus 500. Whether each of the at least one X-ray detector 610, 620, or 630 receives power from the X-ray apparatus 500 may vary according to each situation of the at least one X-ray detector 610, 620, or 630.

When the at least one X-ray detector 610, 620, or 630 receives power from the X-ray apparatus 500, the X-ray apparatus 500 may supply power to the X-ray detector that is determined to be the power consumption mode, and may interrupt or reduce the power supplied to the X-ray detector that is determined to be the power save mode. For example, the supply of power to the X-ray detector may be continued or discontinued through turning on/off of a switch device of the X-ray apparatus 500. Accordingly, the X-ray detector may be operated according to the power mode determined by the X-ray apparatus 500.

Alternatively, the X-ray apparatus 500 may transmit a signal indicating the determined power mode to each of the at least one X-ray detector 610, 620, or 630. The X-ray apparatus 500 may transmit a signal indicating the power consumption mode to the X-ray detector determined to be the power consumption mode and a signal indicating the power save mode to the X-ray detector determined to be the power save mode. The X-ray detector may operate according to the power mode based on the received signal. In other words, the X-ray detector that received the signal indicating the power consumption mode may operate in the power consumption mode and the X-ray detector that received the signal indicating the power save mode may operate in the power save mode.

It is assumed in FIG. 5 that the first X-ray detector 610 receives power separately from the X-ray apparatus 500, and the second X-ray detector 620 and the third X-ray detector 630 receive power from the X-ray apparatus 500. In this case, the X-ray apparatus 500 may supply power to the second X-ray detector 620 and may interrupt or reduce the power supplied to the third X-ray detector 630. Also, the X-ray apparatus 500 may transmit a signal indicating the power save mode to the first X-ray detector 610. Accordingly, the second X-ray detector 620 may operate in the power consumption mode, and the first X-ray detector 610 and the third X-ray detector 630 may operate in the power save mode.

Figure 6:
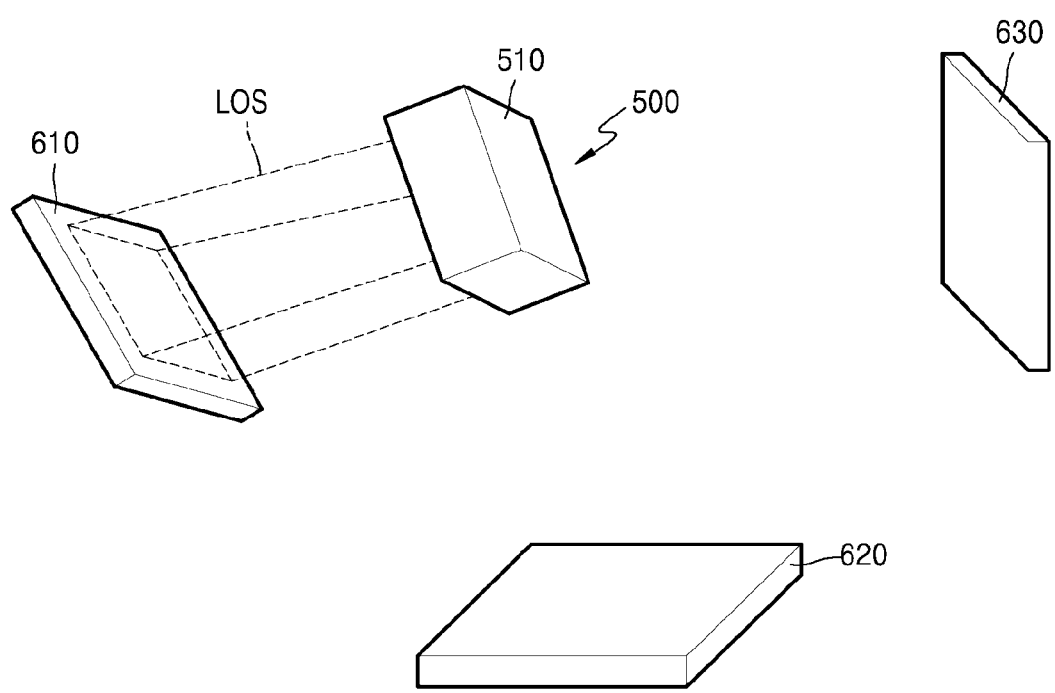
FIG. 6 illustrates an example of a case in which the X-ray apparatus selects a first X-ray detector.

FIG. 6 illustrates an example of a case in which the X-ray apparatus 500 selects the first X-ray detector 610.

Referring to FIG. 6, the X-ray apparatus 500 may select the first X-ray detector 610 facing the X-ray radiator 510, based on the orientation information of the X-ray radiator 510 and the orientation information of the at least one X-ray detector 610, 620, or 630. The X-ray apparatus 500 may determine the power mode of the first X-ray detector 610 that is selected, to be the power consumption mode. The X-ray apparatus 500 may determine the power modes of the second X-ray detector 620 and the third X-ray detector 630 that are not selected, to be the power save mode.

Figure 7:
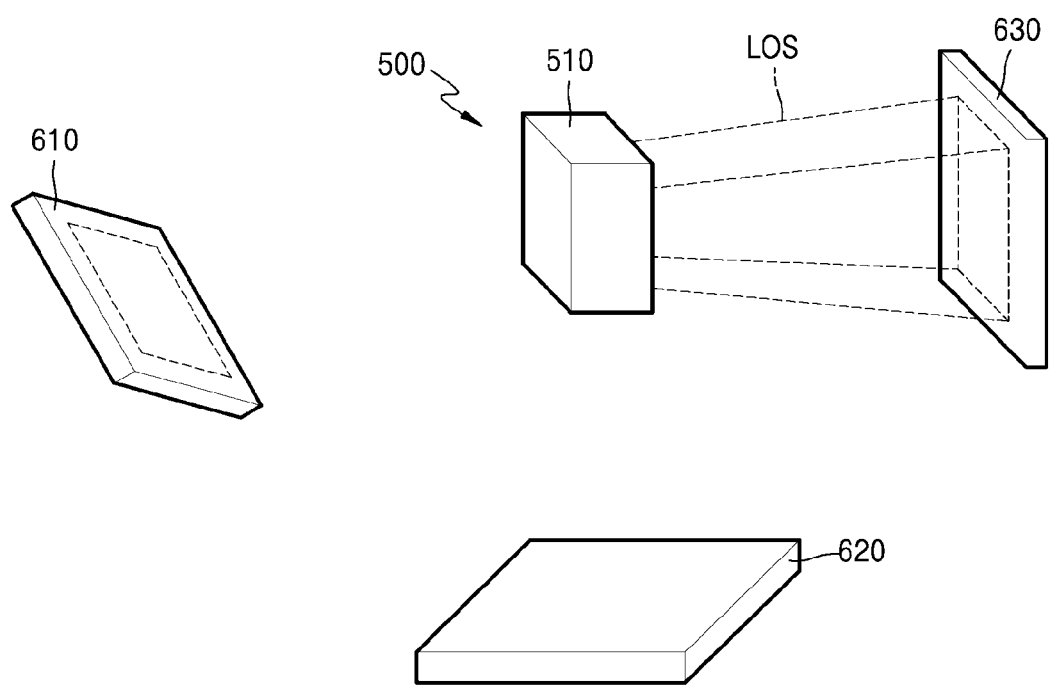
FIG. 7 illustrates an example of a case in which the X-ray apparatus selects a third X-ray detector.

FIG. 7 illustrates an example of a case in which the X-ray apparatus 500 selects the third X-ray detector 630.

Referring to FIG. 7, the X-ray apparatus 500 may select the third X-ray detector 630 facing the X-ray radiator 510, based on the orientation information of the X-ray radiator 510 and the orientation information of the at least one X-ray detector 610, 620, or 630. The X-ray apparatus 500 may determine the power mode of the third X-ray detector 630 that is selected, to be the power consumption mode. The X-ray apparatus 500 may determine the power modes of the first X-ray detector 610 and the second X-ray detector 620 that are not selected, to be the power save mode.

As such, the X-ray apparatus 500 may select the at least one X-ray detector 610, 620, or 630, and determine the power mode of the selected X-ray detector, to be the power consumption mode, and the power mode of an X-ray detector that is not selected, to be the power save mode. Thus, the power unnecessarily consumed by the X-ray apparatus 500 and the at least one X-ray detector 610, 620, or 630 may be reduced.

Figure 8:
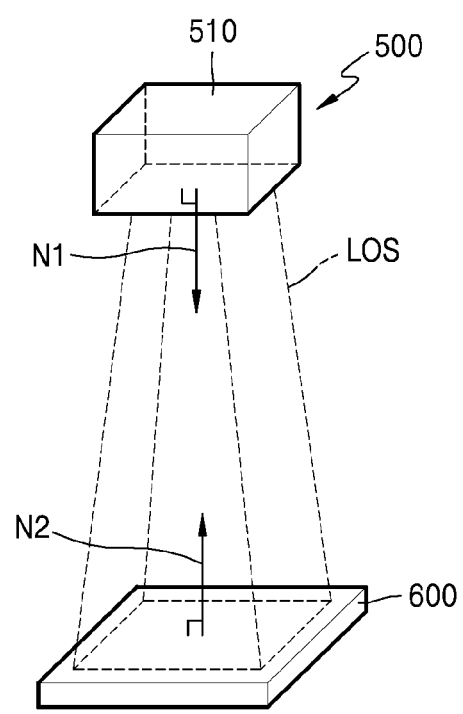
FIG. 8 illustrates an example of orientation information acquired by an X-ray apparatus according to an exemplary embodiment.

FIG. 8 illustrates an example of orientation information acquired by the X-ray apparatus 500 of FIG. 5. In FIG. 8, only one X-ray detector 600 is illustrated disposed around the X-ray apparatus 500. However, such an arrangement is merely for convenience of explanation, and the number of X-ray detectors disposed around the X-ray apparatus 500 is not limited thereto.

Referring to FIG. 8, the X-ray apparatus 500 may acquire the orientation information of the X-ray radiator 510 and the orientation information of the X-ray detector 600. The orientation information may include at least one of positional information and directional information.

The positional information of the X-ray radiator 510 may include information such as coordinates (x, y, z), but is not limited thereto.

The directional information of the X-ray radiator 510 may include information about an X-ray radiation direction or LOS of the X-ray radiator 510. Alternatively, the directional information of the X-ray radiator 510 may include information indicating a normal line N1 of the X-ray radiator 510. Also, the directional information of the X-ray radiator 510 may include an angle formed between the X-ray radiator 510 and a vertical plane or a horizontal plane. However, the present exemplary embodiment is not limited thereto.

The positional information of the X-ray detector 600 may include information such as coordinates (x, y, z), but is not limited thereto.

The directional information of the X-ray detector 600 may include information about whether the LOS of the X-ray radiator 510 is located above the X-ray detector 600. Alternatively, the directional information of the X-ray detector 600 may include information indicating a degree of matching between the LOS of the X-ray radiator 510 and the X-ray detector 600. For example, the degree of matching may be related to an area of the LOS of the X-ray radiator 510 on the X-ray detector 600. The directional information of the X-ray detector 600 may include information indicating a normal line N2 of the X-ray detector 600. Alternatively, the directional information of the X-ray detector 600 may include an angle formed between the X-ray detector 600 and a vertical plane or a horizontal plane. However, the present exemplary embodiment is not limited thereto.

The X-ray apparatus 500 may further include an orientation information acquirer (not shown) acquiring orientation information of at least one of the X-ray radiator 510 and the X-ray detector 600. For example, the orientation information acquirer may include an imaging apparatus, a laser light source, a gyroscope, an inertial measurement unit (IMU), an accelerometer, a magnetometer, a GPS sensor, etc. However, the present exemplary embodiment is not limited thereto. The orientation information acquirer may acquire orientation information of at least one of the X-ray radiator 510 and the X-ray detector 600 in a variety of methods using light, electric waves, acoustic waves, a magnetic field, an electric file, etc.

The X-ray detector 600 may also include an orientation information acquirer (not shown) acquiring the orientation information of at least one of the X-ray radiator 510 and the X-ray detector 600. The X-ray detector 600 may transmit the orientation information acquired by the orientation information acquirer, to the X-ray apparatus 500. The X-ray detector 600 may transmit the orientation information in a variety of methods such as a wired or wireless method. To this end, each of the X-ray apparatus 500 and the X-ray detector 600 may further include a communicator (not shown).

The X-ray apparatus 500 may select the X-ray detector 600, based on the orientation information of the X-ray radiator 510 and the orientation information of the X-ray detector 600.

In an example, the X-ray apparatus 500 may select the X-ray detector 600 that meets the LOS of the X-ray radiator 510. In other words, when the LOS of the X-ray radiator 510 is located above the X-ray detector 600, the X-ray apparatus 500 may select the X-ray detector 600.

In another example, the X-ray apparatus 500 may select the X-ray detector 600, based on a degree of matching between the normal line N1 of the X-ray radiator 510 and the normal line N2 of the X-ray detector 600. Alternatively, the X-ray apparatus 500 may select the X-ray detector 600, based on a degree of alignment to the X-ray radiator 510. The degree of alignment to the X-ray radiator 510 may be acquired based on at least one of a distance between the X-ray radiator 510 and the X-ray detector, a degree of parallelism between the X-ray radiator 510 and the X-ray detector, and a degree of matching between a center of the X-ray radiator 510 and a center of the X-ray detector 600.

As such, the X-ray apparatus 500 may select the X-ray detector 600 facing the X-ray radiator 510 in a variety of methods. However, the method of selecting the X-ray detector 600 is not limited thereto.

According to the present exemplary embodiment, the X-ray detector 600 may be coupled to the receptors 280 and 290 of FIG. 2, or may not be coupled thereto. Next, a case in which the X-ray detector is coupled to the receptor and a case in which the X-ray detector is not coupled to the receptor are described with reference to FIG. 9.

Figure 9:
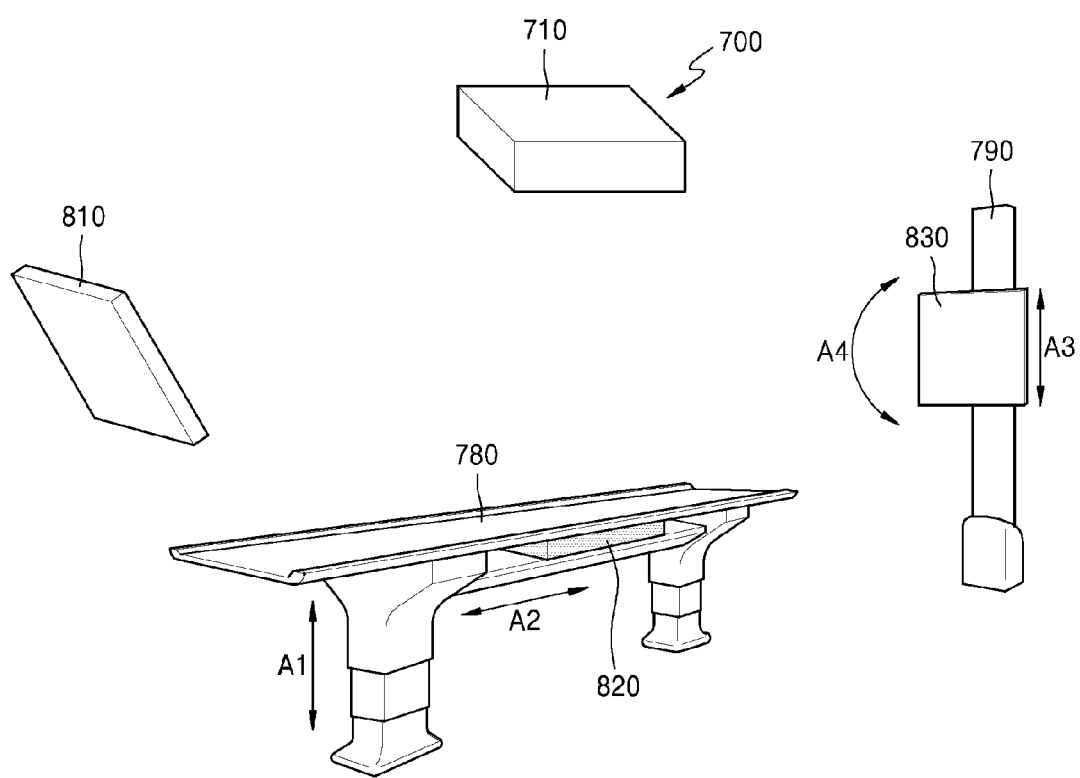
FIG. 9 illustrates an X-ray apparatus according to an exemplary embodiment.

FIG. 9 illustrates an X-ray apparatus 700 according to an exemplary embodiment. The X-ray apparatus 700 of FIG. 9 may be some exemplary embodiments of the above-described X-ray apparatus 500.

Referring to FIG. 9, X-ray detectors 810, 820, and 830 existing around the X-ray apparatus 700 may be coupled to receptors 780 and 790 or may not be coupled thereto. The receptors 780 and 790 may be connected to the X-ray apparatus 700 in a variety of methods such as a wired or wireless method. Although FIG. 9 illustrates that the receptors 780 and 790 are devices that are disposed separately from the X-ray apparatus 700, the receptors 780 and 790 may be included in the X-ray apparatus 700.

In FIG. 9, the first X-ray detector 810 is a portable X-ray detector that may exist at a certain position without being coupled to any receptor. The second X-ray detector 820 is coupled to the receptor 780 that is a table type. The third X-ray detector 830 is coupled to the receptor 790 that is a stand type. However, FIG. 9 is merely an example and does not limit whether the X-ray detectors 810, 820, and 830 disposed around the X-ray apparatus 700 and the receptors 780 and 790 are coupled to each other. In particular, although FIG. 9 illustrates that the first X-ray detector 810 is the only one portable X-ray detector, the portable X-ray detector may not exist or a plurality of portable X-ray detectors may exist.

The position and direction of the receptors 780 and 790 may be fixed or changed within a predetermined range.

The table type receptor 780 may include an actuator (not shown). The actuator may move the table type receptor 780 in a first direction A1. Accordingly, the height of the second X-ray detector 820 coupled to the table type receptor 780 may be adjusted. Also, the actuator may move the second X-ray detector 820 in a second direction A2. In other words, while the direction of the table type receptor 780 may be fixed, the position of the table type receptor 780 may be changed only within a predetermined range due to the movement in the first direction A1 or the second direction A2.

The stand type receptor 790 may also include an actuator (not shown). The actuator may move the third X-ray detector 830 coupled to the stand type receptor 790 in a third direction A3. Accordingly, the height of the third X-ray detector 830 may be adjusted. Also, the actuator may rotate the third X-ray detector 830 in a fourth direction A4. In other words, while the direction of the stand type receptor 790 may be changed within a predetermined range according to the rotation in the fourth direction A4, the position of the stand type receptor 790 may be changed within a predetermined range according to the movement in the third direction A3.

As such, each of the receptors 780 and 790 may include an actuator that may linearly move or rotate the X-ray detectors 820 and 830 respectively coupled to the receptors 780 and 790. For example, the actuator may include a motor (not shown) and a motor driver (not shown) for driving the motor. In the following description, the term "movement" may be interpreted as a concept including both linear movement and rotation.

Also, each of the receptors 780 and 790 may include a power supplier (not shown). The power supplier may provide power to the actuator and the X-ray detectors 820 and 830 coupled thereto. The power supplier may receive power from the X-ray apparatus 700 or from the outside.

In FIG. 9, an X-ray radiator 710 faces the second X-ray detector 820 coupled to the table type receptor 780. Accordingly, the X-ray apparatus 700 may select the second X-ray detector 820, based on the orientation information of the X-ray radiator 710 and the orientation information of the X-ray detectors 810, 820, and 830. Accordingly, the X-ray apparatus 700 may determine a power mode of the second X-ray detector 820 to be the power consumption mode, and the power modes of the first X-ray detector 810 and the third X-ray detector 830 to be the power save mode.

The orientation information of the X-ray detectors 810, 820, and 830 may include information indicating whether the X-ray detectors 810, 820, and 830 are coupled to the receptors 780 and 790. Since the position and direction of the receptors 780 and 790 are fixed or changed in a predetermined range, the position and direction of the X-ray detector coupled to the receptors 780 and 790 may be fixed or changed only within a predetermined range. Accordingly, whether the X-ray detectors 810, 820, and 830 are coupled to the receptors 780 and 790 may indicate the orientation of the X-ray detectors 810, 820, and 830.

The orientation information of the second X-ray detector 820 may include information indicating that the second X-ray detector 820 is coupled to the table type receptor 780. The orientation information of the third X-ray detector 830 may include information indicating that the third X-ray detector 830 is coupled to the stand type receptor 790. The orientation information of the first X-ray detector 810 may include information indicating that the first X-ray detector 810 is not coupled to any receptor. Alternatively, the orientation information of the first X-ray detector 810 may include information indicating that the first X-ray detector 810 is a portable X-ray detector.

The orientation information of the X-ray radiator 710 may be acquired based on a positioning mode of the X-ray apparatus 700. The positioning mode of the X-ray apparatus 700 may include a stand mode, a table mode, and a portable mode. When the positioning mode of the X-ray apparatus 700 is a table mode, the X-ray radiator 710 may face the table type receptor 780. When the positioning mode of the X-ray apparatus 700 is a stand mode, the X-ray radiator 710 faces the stand type receptor 790. When the positioning mode of the X-ray apparatus 700 is a portable mode, the X-ray radiator 710 may face the third X-ray detector 830 that is a portable X-ray detector. Accordingly, the X-ray apparatus 700 may acquire the orientation information of the X-ray radiator 710 based on the positioning mode.

The X-ray apparatus 700 may determine the power modes of the receptors 780 and 790 identically to the determined power modes of the X-ray detectors 820 and 830 coupled to the receptors 780 and 790. In other words, the X-ray apparatus 700 may determine the power mode of the receptor coupled to the X-ray detector that is determined to be in the power save mode, to be the power save mode, and the power mode of the receptor coupled to the X-ray detector that is determined to be in the power consumption mode, to be the power consumption mode.

Accordingly, in FIG. 9, the X-ray apparatus 700 may determine the power mode of the table type receptor 780 coupled to the second X-ray detector 820 that is determined to be in the power consumption mode, to be the power consumption mode, and the power mode of the stand type receptor 790 coupled to the third X-ray detector 830 that is determined to be in the power save mode, to be the power save mode. The X-ray apparatus 700 may interrupt or reduce the power supplied to the stand type receptor 790, or may transmit a signal indicating the power save mode to the stand type receptor 790. Accordingly, the stand type receptor 790 may operate in the power save mode. When the stand type receptor 790 operates in the power save mode, power consumption by the actuator or power supplier included in the stand type receptor 790 may be prevented.

Figure 10:
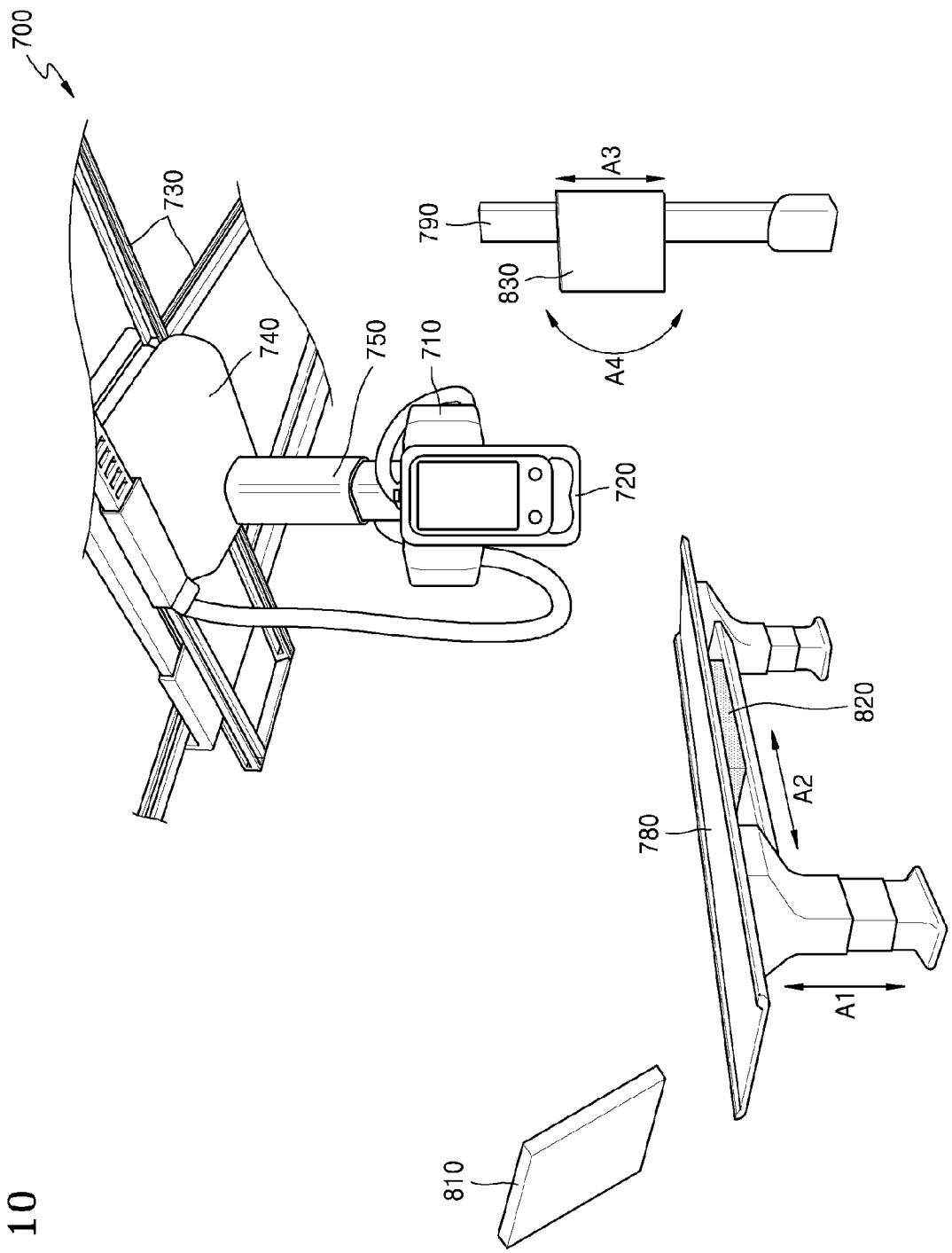
FIG. 10 illustrates an X-ray apparatus according to an exemplary embodiment.

FIG. 10 illustrates an X-ray apparatus 700 according to an exemplary embodiment. The X-ray apparatus 700 of FIG. 10 may be some exemplary embodiments of the X-ray apparatus 700 of FIG. 9.

Referring to FIG. 10, the X-ray apparatus 700 may include the X-ray radiator 710 and a manipulator 720. The manipulator 720 may have an interface for manipulating the X-ray apparatus 700 and may include an input unit and an output unit. Since the manipulator 720 corresponds to the manipulator 140 of FIG. 1, a description thereof will not be repeated here.

The X-ray apparatus 700 may include a guide rail 730, a moving carriage 740, and a post frame 750 which are provided to linearly move the X-ray radiator 710. Since the guide rail 730, the moving carriage 740, and the post frame 750 respectively correspond to the guide rail 220, the moving carriage 230, and the post frame 240 of FIG. 2, descriptions thereof will not be repeated here.

The X-ray apparatus 700 may rotate the X-ray radiator 710. To this end, a rotating joint corresponding to the rotating joint 250 of FIG. 2 may be arranged between the X-ray radiator 710 and the post frame 740.

The X-ray apparatus 700 may include an actuator (not shown) that may linearly move or rotate the X-ray radiator 710. For example, the actuator may include a motor (not shown) and a motor driver (not shown) for driving the motor.

The manipulator 720 of the X-ray apparatus 700 may receive a user's input indicating a positioning mode of the X-ray apparatus 700. Alternatively, a workstation (not shown) that is connected to the X-ray apparatus 700 and controls the X-ray apparatus 700 may receive the user's input indicating a positioning mode of the X-ray apparatus 700.

The X-ray apparatus 700 may determine the positioning mode of the X-ray apparatus 700 from among a stand mode, a table mode, and a portable mode, based on the user's input received by the manipulator 720 or the workstation.

When the positioning mode of the X-ray apparatus 700 is a table mode, the X-ray apparatus 700 may linearly move or rotate the X-ray radiator 710 such that the X-ray radiator 710 faces the table type receptor 780. The X-ray apparatus 700 may automatically move the X-ray radiator 710 such that the X-ray radiator 710 faces the table type receptor 780.

When the positioning mode of the X-ray apparatus 700 is a stand mode, the X-ray apparatus 700 may linearly move or rotate the X-ray radiator 710 such that the X-ray radiator 710 faces the stand type receptor 790. The X-ray apparatus 700 may automatically move the X-ray radiator 710 such that the X-ray radiator 710 faces the stand type receptor 790.

When the positioning mode of the X-ray apparatus 700 is a portable mode, the X-ray apparatus 700 may linearly move or rotate the X-ray radiator 710 such that the X-ray radiator 710 faces the first X-ray detector 810 that is a portable X-ray detector. The movement of the X-ray radiator 710 may be performed manually by the user. Alternatively, at least one of the X-ray apparatus 700 and the workstation may receive information about the movement of the X-ray radiator 710, and may move the X-ray radiator 710 based on the received information. Otherwise, the X-ray apparatus 700 may acquire orientation information of the first X-ray detector 810 and automatically move the X-ray radiator 710 based on the acquired orientation information, thereby allowing the X-ray radiator 710 to face the first X-ray detector 810.

Figure 11:
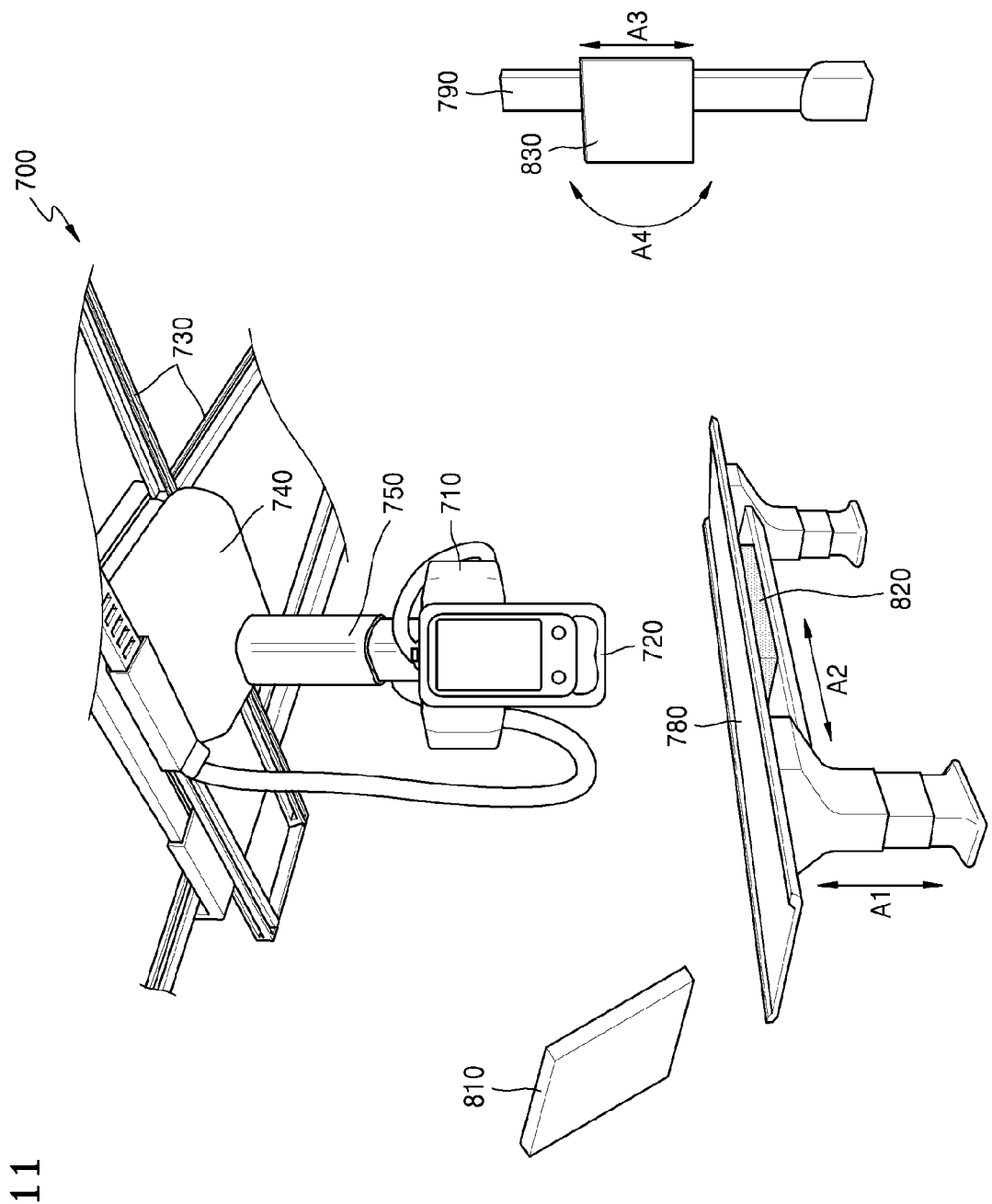
FIG. 11 illustrates an example of an operation performed when a positioning mode of the X-ray apparatus of FIG. 10 is determined to be a table mode.

FIG. 11 illustrates an example of an operation performed when the positioning mode of the X-ray apparatus 700 of FIG. 10 is determined to be a table mode.

Referring to FIGS. 10 and 11, the X-ray apparatus 700 that is determined to be in a table mode may move the guide rail 730, the moving carriage 740, and the post frame 750 such that the X-ray radiator 710 faces the table type receptor 780. Accordingly, the X-ray radiator 710 may move from the orientation of FIG. 10 to the orientation of FIG. 11.

The X-ray apparatus 700 may acquire the orientation information of the X-ray radiator 710, based on the positioning mode being a table mode. Also, the X-ray apparatus 700 may acquire the orientation information of the second X-ray detector 820 including information indicating the second X-ray detector 820 is coupled to the table type receptor 780.

The X-ray apparatus 700 may select the second X-ray detector 820 of the first to third X-ray detectors 810, 820, and 830, based on the orientation information of the X-ray radiator 710 and the orientation information of the second X-ray detector 820. The X-ray apparatus 700 may determine the power mode of the second X-ray detector 820 to be the power consumption mode and the power modes of the X-ray detectors 810 and 830 to be the power save mode. Also, the X-ray apparatus 700 may determine the power mode of the stand type receptor 790 coupled to the third X-ray detector 830, to be the power save mode.

Figure 12A:
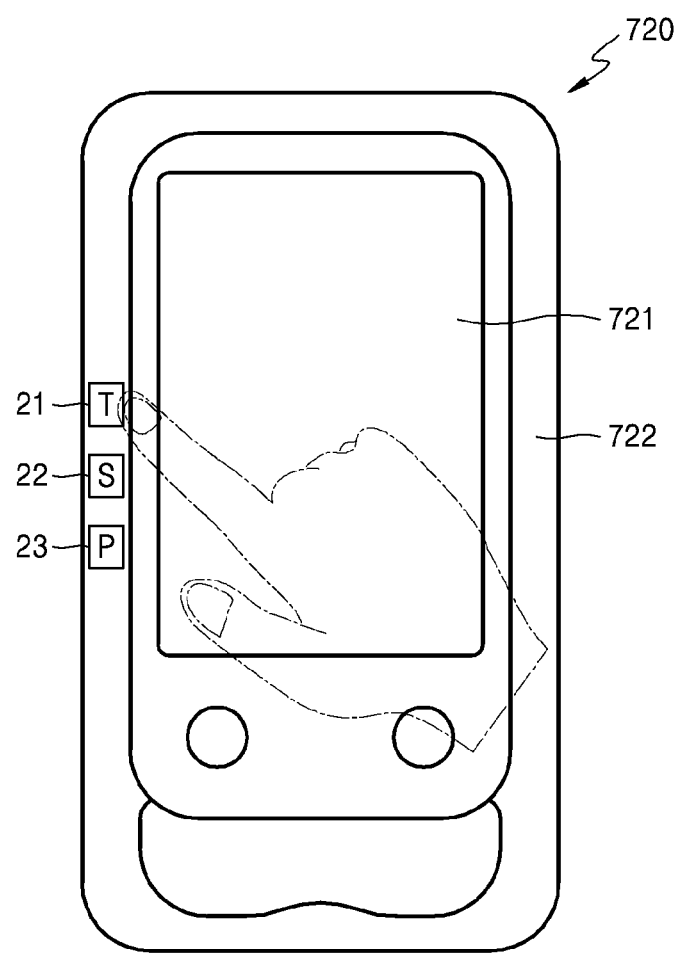
FIGS. 12A and 12B illustrate examples of a manipulator included in the X-ray apparatus of FIG. 11.
Figure 12B:
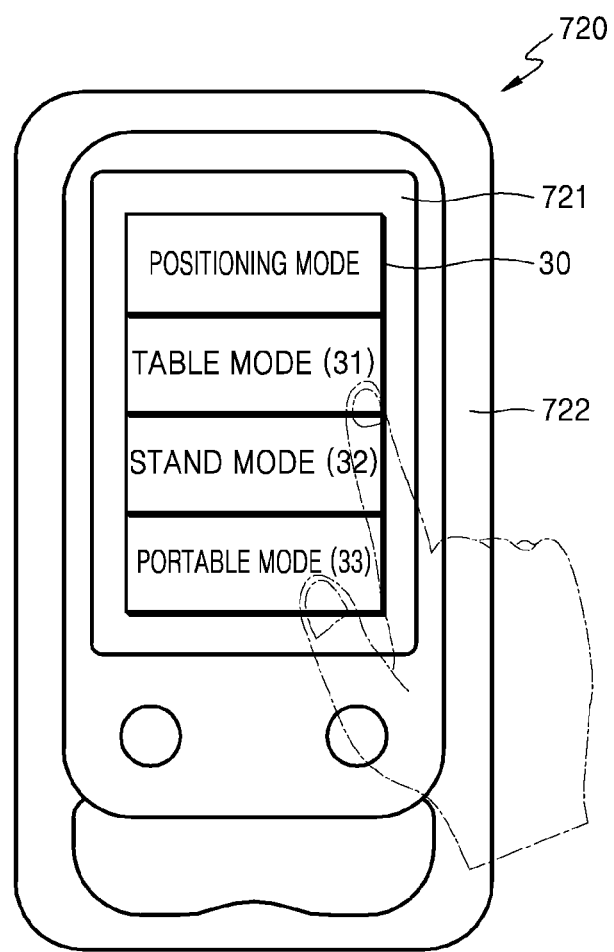

FIGS. 12A and 12B illustrate examples of the manipulator 720 included in the X-ray apparatus 700 of FIG. 11.

Referring to FIGS. 11, 12A, and 12B, the manipulator 720 may include an output unit 721 and an input unit 722. The input unit 722 signifies a unit for inputting data for the user to control the X-ray apparatus 700. The input unit 722 may receive user's inputs of commands for controlling the X-ray apparatus 700 and various pieces of information about X-ray imaging. Although FIGS. 12A and 12B illustrate that the output unit 721 and the input unit 722 included in the manipulator 720 are separated from each other, the present exemplary embodiment is not limited thereto. The input unit 722 or a part of the input unit 722 may be embodied in the output unit 721. For example, when the input unit 722 includes a touch screen, the touch screen may be embodied in the output unit 721.

Referring to FIG. 12A, the input unit 722 may include buttons 21 to 23 to select respective positioning modes. The first button 21 may correspond to a table mode, the second button 22 may correspond to a stand mode, and the third button 23 may correspond to a portable mode. When the input unit 722 receives a user's input for selecting one of the buttons 21-23, the X-ray apparatus 700 may determine the positioning mode to be a positioning mode corresponding to the selected button. For example, when the user selects the first button 21, the X-ray apparatus 700 may determine the positioning mode to be a table mode.

Referring to FIG. 12B, the output unit 721 may output on a screen a user interface (UI) 30 through which the user may select one of the positioning modes. The user may select one of a table mode 31, a stand mode 32, and a portable mode 33, through the UI 30. For example, when the user selects the table mode 31, the X-ray apparatus 700 may determine the positioning mode to be a table mode.

Although FIGS. 12A and 12B illustrate examples of the method of selecting a positioning mode of the X-ray apparatus 700 by the user, the present exemplary embodiment is not limited thereto.

Figure 13:
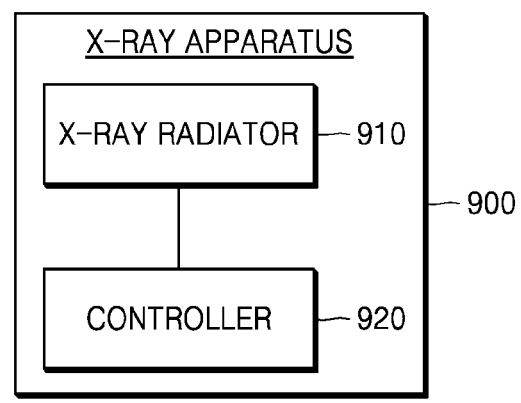
FIG. 13 is a block diagram illustrating a structure of an X-ray apparatus according to an exemplary embodiment.

FIG. 13 is a block diagram illustrating a structure of an X-ray apparatus 900 according to an exemplary embodiment.

Referring to FIG. 13, the X-ray apparatus 900 may include an X-ray radiator 910 and a controller 920. The above-described contents may be applied to the respective corresponding elements of the X-ray apparatus 900.

The X-ray radiator 910 may be configured to radiate an X-ray.

The controller 920 may acquire orientation information of the X-ray radiator 910 and orientation information of at least one X-ray detectors. The controller 920 may select one of the at least one X-ray detector, based on the orientation information of the X-ray radiator 910 and the orientation information of the at least one X-ray detector. The controller 920 may determine the power mode of the selected X-ray detector to be the power consumption mode. The controller 920 may determine the power modes of the X-ray detectors that are not selected to be the power save mode.

If there is any X-ray detector that is coupled to a receptor, the controller 920 may determine the power mode of the receptor to be the same as the power mode of the X-ray detector coupled to the receptor.

The orientation information of at least one X-ray detector may include information indicating whether the at least one X-ray detector is coupled to the receptor.

The controller 920 may acquire the orientation information of the X-ray radiator 910 based on the positioning mode including the stand mode, the table mode, and the portable mode.

The X-ray apparatus 900 may further include an input unit, for example, the input unit 722 of FIG. 12, for receiving a user's input for selecting the positioning mode.

Alternatively, the X-ray apparatus 900 may further include an orientation information acquirer (not shown) for acquiring at least one of the orientation information of the X-ray radiator 910 and the orientation information of at least one X-ray detector. Each X-ray detector may also include the orientation information acquirer that acquires at least one of the orientation information of the X-ray radiator 910 and the orientation information of the X-ray detector itself. Since the orientation information acquirer has already been described with reference to FIG. 8, a detailed description thereof will not be repeated here.

As such, as the X-ray apparatus 900 determines the power mode of each of X-ray detector, unnecessary power consumption may be prevented. According to the present exemplary embodiment, since only the X-ray detector selected to be used for imaging is operated in the power consumption mode and the other X-ray detectors are operated in the power save mode, unnecessary power consumption in an X-ray system, for example, the X-ray system 1000 of FIG. 1, may be generally reduced. Also, as the receptor, to which the X-ray detector that is determined to be in the power save mode is coupled, is also operated in the power save mode, power consumption may be reduced. The X-ray apparatus 900 according to the present exemplary embodiment may differently determine the power mode of each element to be, for example, the power consumption mode or the power save mode. Accordingly, such elements as the X-ray detector or the receptor that are included in or connected to the X-ray apparatus 900 may be operated in the power mode suitable for the purpose of each element. Thus, energy efficiency may be improved.

The X-ray apparatus 900 according to the present exemplary embodiment may be operated in one of a plurality of operation modes. The operation mode may include a sleep mode and a use mode.

The sleep mode may be referred to be a low power mode. The sleep mode may be an operation mode in which the X-ray apparatus 900 consumes a minimum amount of power.

The use mode may be an operation mode in which the X-ray apparatus 900 prepares to scan an object or scans the object. The term "scan" may refer to X-ray imaging.

The use mode may include a scan mode in which the X-ray apparatus 900 scans an object to generate a medical image, and a ready-to-scan mode that is a state between each scanning. In the scan mode, the X-ray apparatus 900 may perform preparing radiation of an X-ray, radiating an X-ray, etc. Also, in the scan mode, the X-ray apparatus 900 may perform a mechanical movement of the X-ray apparatus 900 such as a movement of the X-ray radiator 910, a movement of the receptor, etc.

The operation mode may further include an off mode in addition to the sleep mode and the use mode. The off mode is an operation mode in which the X-ray apparatus 900 is turned off and thus the X-ray apparatus 900 does not consume power.

The controller 920 may determine the operation mode of the X-ray apparatus 900, and may control the X-ray apparatus 900 to operate according to the determined operation mode. The power consumption of the X-ray apparatus 900 may increase in an order of the off mode, the sleep mode, the ready-to-scan mode, and the scan mode.

In the above-described exemplary embodiment, when the X-ray apparatus 900 determines the power mode of each of the X-ray detectors, the X-ray apparatus 900 may be operated in the use mode. In this state, the X-ray apparatus 900 may be operated in the ready-to-scan mode of the use mode.

According to the present exemplary embodiment, the controller 920 may set a condition for switching the operation mode of the X-ray apparatus 900 to the sleep mode.

The controller 920 may set a threshold time as the condition for switching the operation mode of the X-ray apparatus 900 to the sleep mode. When a non-usage time of the X-ray apparatus 900 exceeds the threshold time, the controller 920 may switch the operation mode to the sleep mode. For example, when the X-ray apparatus 900 does not receive a user input for a set threshold time, the controller 920 may determine that the non-usage time of the X-ray apparatus 900 exceeds the threshold time. Although examples of the user input may include a command for manipulating the X-ray apparatus 900 and various pieces of information about X-ray imaging, the present exemplary embodiment is not limited thereto.

When the X-ray apparatus 900 is connected to the workstation, and both the X-ray apparatus 900 and the workstation are not in use for the set threshold time, the controller 920 may switch the operation mode to the sleep mode. The workstation may also be switched to the sleep mode.

The controller 920 according to the present exemplary embodiment may set the threshold time for switching the operation mode to the sleep mode based on the user's input.

Alternatively, the controller 920 according to the present exemplary embodiment may adaptively set the threshold time for switching the operation mode to the sleep mode. The controller 920 may adaptively set the threshold time through a method of learning a use pattern of the X-ray apparatus 900 with respect to a user. For example, after setting an initial threshold time according to a user's input, the controller 920 may update the threshold time from the initial threshold time through learning of a use pattern of the X-ray apparatus 900. To this end, the controller 920 may monitor a usage time and a non-usage time of the X-ray apparatus 900. The controller 920 may acquire a "usage time distribution function" as a result of the monitoring.

Figure 14:
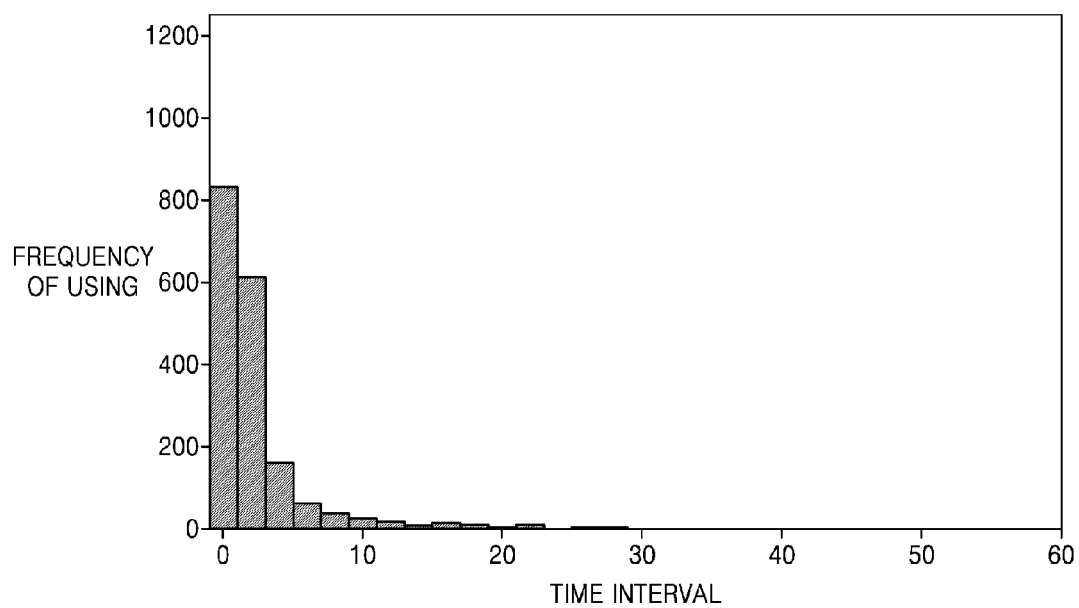
FIG. 14 is an example of a usage time distribution function acquired by the X-ray apparatus of FIG. 13.

FIG. 14 is an example of a usage time distribution function acquired by the X-ray apparatus 900 of FIG. 13.

Referring to FIGS. 13 and 14, a usage time distribution function is a frequency of using the X-ray apparatus 900 with respect to a time interval between scanning operations performed by the X-ray apparatus 900. The controller 920 may acquire the usage time distribution function by monitoring a usage time and a non-usage time of the X-ray apparatus 900 for a predetermined time. The controller 920 may acquire a threshold time to enter the sleep mode based on the usage time distribution function.

When the usage time distribution function is referred to as D(t), the controller 920 may acquire a utility function E(t0) as follows based on the usage time distribution function D(t).

$$E(t_0) = -w1 \cdot \int_0^\infty D(t)dt + w2 \int_{t_0}^\infty t \cdot D(t)dt \quad \text{[Equation 1]}$$

In Equation 1, "w1" is a first weight and "w2" is a second weight. The utility function E(t0) may vary according to a time "t0". The controller 920 may acquire the time t0 for maximizing the utility function E(t0). The controller 920 may set the time t0 for maximizing the utility function E(t0) as the threshold time to enter the sleep mode.

The controller 920 according to the present exemplary embodiment may continuously update the acquired usage time distribution function D(t) by continuously monitoring the usage time and the non-usage time of the X-ray apparatus 900.

When the controller 920 acquires the usage time distribution function D(t) that is continuously updated, the threshold time may be also updated as the utility function E(t0) varies. In this case, the controller 920 may reset the threshold time to enter the sleep mode as an updated threshold time. The controller 920 may periodically update the usage time distribution function D(t), the utility function E(t0), and the threshold time.

Accordingly, the X-ray apparatus 900 according to the present exemplary embodiment may optimize the threshold time by adaptively setting the threshold time that is the time to enter the sleep mode. The optimal threshold time may vary according to a situation such as a time when or a place where the X-ray apparatus 900 is used. For example, a usage time distribution function of the X-ray apparatus 900 arranged in a general scanning room and a usage time distribution function of the X-ray apparatus 900 arranged in an emergency room may differ from each other. Also, as the X-ray apparatus 900 is used for a long time, the usage time distribution function may vary as well.

Accordingly, when the threshold time is adaptively set by continuously updating the usage time distribution function of the X-ray apparatus 900 according to the present exemplary embodiment threshold time, the controller 920 may acquire the optimal threshold time.

A certain degree of a transit time may be necessary when the controller 920 switches the operation mode of the X-ray apparatus 900 from the sleep mode to the use mode. However, when the threshold time is too short, the X-ray apparatus 900 may frequently switch the operation mode to the sleep mode. A user may be inconvenienced during the transit time during which the operation mode is changed from the sleep mode to the use mode. When the threshold time is too long, the X-ray apparatus 900 may consume unnecessary power. Accordingly, according to the present exemplary embodiment, when the optimal threshold time is set by analyzing a use pattern of the X-ray apparatus 900, efficiency of power consumption may be maximized.

The controller 920 according to the present exemplary embodiment may further set other conditions for switching the operation mode to the sleep mode in addition to the setting of the threshold time. For example, the controller 920 may set the condition for entering the sleep mode based on the user's input. The controller 920 may receive from the user, as the user's input, a time section when a frequency of using the X-ray apparatus 900 is not high, such as a lunch time or a night time. In the time section, the controller 920 may switch the operation mode to the sleep mode. As such, the X-ray apparatus 900 may enter the sleep mode according to the scheduling of a user. In other words, the user may set or adjust the sleep mode entering condition of the X-ray apparatus 900.

Also, the X-ray apparatus 900 may further include a sensor. The sensor may include a sensor that may sense a user or an object. For example, the sensor may be a position sensing device (PSD). However, the present exemplary embodiment is not limited thereto. When the sensor senses the user or object, the controller 920 may be operated in the use mode. When the user or object is not sensed for a predetermined set time, the controller 920 may be operated in the sleep mode.

Alternatively, the sensor may include a sensor that may sense illumination. For example, when the illumination is equal to or less than a threshold value, the controller 920 may be operated in the sleep mode. Alternatively, when the illumination is equal to or greater than the threshold value, the controller 920 may be operated in the use mode.

When the X-ray apparatus 900 operating in the sleep mode receives a user's input or the sensor senses a specific condition, the controller 920 may switch the operation mode from the sleep mode to the use mode. The sensor included in the X-ray apparatus 900 operating in the sleep mode may perform a minimum sensing operation.

As such, when the specific condition is met, the X-ray apparatus 900 according to the present exemplary embodiment is switched to the sleep mode and thus energy consumption may be reduced. Also, as the X-ray apparatus 900 adaptively sets the threshold time to switch the operation mode to the sleep mode, an optimal threshold time may be acquired.

Figure 15:
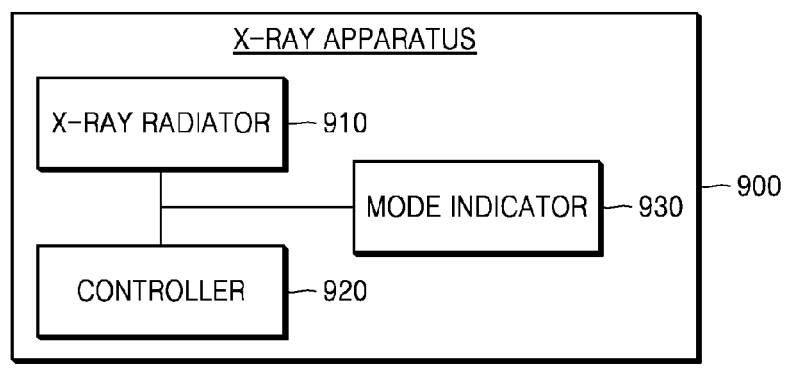
FIG. 15 is a block diagram illustrating another structure of the X-ray apparatus of FIG. 13.

FIG. 15 is a block diagram illustrating another structure of the X-ray apparatus 900 of FIG. 13.

Referring to FIG. 15, the X-ray apparatus 900 may further include a mode indicator 930, in addition to the X-ray radiator 910 and the controller 920.

The mode indicator 930 may indicate a current operation mode of a plurality of operation modes of the X-ray apparatus 900. The mode indicator 930 may be attached on any outside surface of the X-ray apparatus 900 that may be seen by the user. For example, the mode indicator 930 may include a light-emitting element. For example, the light-emitting element may include a light-emitting diode (LED).

For example, the mode indicator 930 may emit light by using a particular method corresponding to the current operation mode. In a detailed example, when the current operation mode of the X-ray apparatus 900 is a sleep mode, the mode indicator 930 may repeat flickering at a speed equal to or less than a predetermined speed. In other words, the light-emitting element of the mode indicator 930 may switch between an on state and an off state at a speed equal to or less than a predetermined speed. As the mode indicator 930 of the X-ray apparatus 900 slowly flickers, the user may intuitively recognize that the X-ray apparatus 900 has entered the sleep mode. When the operation mode of the X-ray apparatus 900 is an off mode, the light-emitting element of the mode indicator 930 may be turned off. When the X-ray apparatus 900 is a use mode, the light-emitting element of the mode indicator 930 may be maintained in an on state without flickering.

Alternatively, as a different color is allotted for each of a plurality of operation modes, the mode indicator 930 may indicate a current operation mode. For example, the sleep mode may correspond to red and the use mode may correspond to blue.

Alternatively, the mode indicator 930 may distinguish only one of the operation modes from the other modes. For example, in the sleep mode only, the mode indicator 930 may indicate that the operation mode of the X-ray apparatus 900 is a sleep mode and, in the other operation modes, the mode indicator 930 may indicate nothing.

However, the above-described operation of the mode indicator 930 is merely exemplary, and the mode indicator 930 may indicate the current operation mode of the X-ray apparatus 900 by using various methods.

Figure 16:
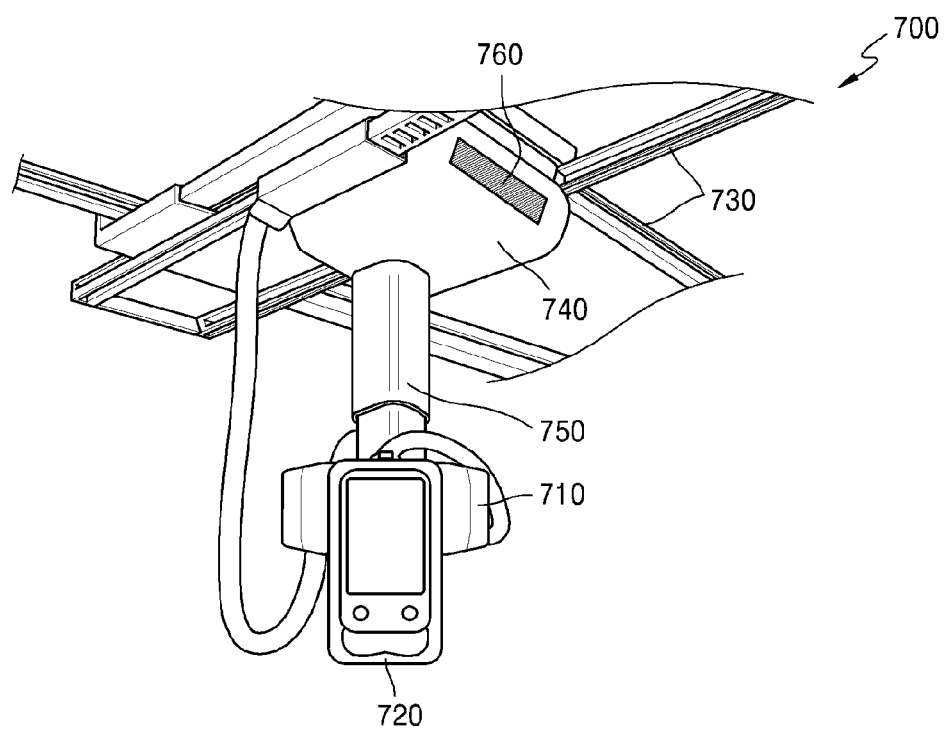
FIG. 16 illustrates an X-ray apparatus including a mode indicator according to an exemplary embodiment.

FIG. 16 illustrates an X-ray apparatus 700 including a mode indicator according to an exemplary embodiment.

Referring to FIG. 16, the X-ray apparatus 700 may include a mode indicator 760. Although the mode indicator 760 is illustrated as being attached on the moving carriage 740, the present exemplary embodiment is not limited thereto. The mode indicator 760 may indicate the current operation mode of the X-ray apparatus 700 by using a variety of methods such as a light-emitting color, a light-emitting frequency, etc. which are described with reference to FIG. 15.

Except that the X-ray apparatus 700 of FIG. 16 further includes the mode indicator 760, since the X-ray apparatus 700 is the same as the X-ray apparatus 700 of FIGS. 10 and 11, a detailed description thereof will not be repeated here.

Part of the operation of the X-ray apparatus 700 according to the present exemplary embodiment may be performed by the workstation. In the following description, a workstation according to an exemplary embodiment is described.

Figure 17:
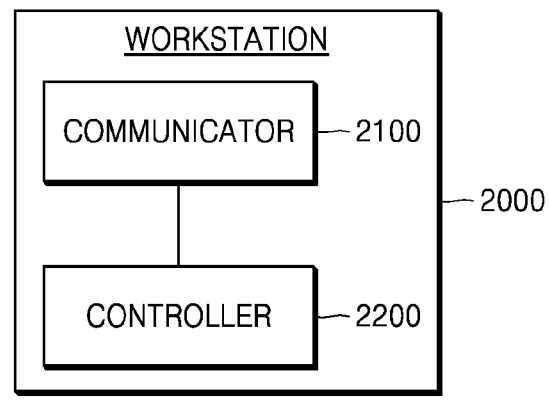
FIG. 17 is a block diagram illustrating a structure of a workstation according to an exemplary embodiment.

FIG. 17 is a block diagram illustrating a structure of the workstation 2000 according to an exemplary embodiment.

Referring to FIG. 17, the workstation 2000 may include a communicator 2100 and a controller 2200. The communicator 2100 is configured to be capable of communicating with external apparatuses such as an X-ray apparatus, an X-ray detector, a server, a portable terminal, etc. The communicator 2100 may include one or more of a NFC module, a wired communication module, and a wireless communication module.

The communicator 2100 may receive orientation information of an X-ray radiator and orientation information of at least one X-ray detector. The communicator 2100 may receive the orientation information of the X-ray radiator from an X-ray apparatus. Also, the communicator 2100 may receive the orientation information of each X-ray detector from the at least one X-ray detector. Alternatively, the communicator 2100 may receive the orientation information of the X-ray radiator and the orientation information of the at least one X-ray detector from the X-ray apparatus.

The controller 2200 may select the at least one X-ray detector based on the orientation information of the X-ray radiator and the orientation information of the at least one X-ray detector. The controller 2200 may determine the power mode of the selected X-ray detector to be the power consumption mode. The controller 2200 may determine the power mode of the X-ray detector that is not selected, to be the power save mode.

The orientation information of the at least one X-ray detector may include information indicating whether the at least one X-ray detector is coupled to a receptor.

When any of the at least one X-ray detector is coupled to the receptor, the controller 2200 may determine the power mode of the receptor to be the same as that of the X-ray detector coupled to the receptor.

The controller 2200 may acquire orientation information of the X-ray radiator based on the positioning mode of the X-ray apparatus, including the stand mode, the table mode, and the portable mode. The workstation 2000 may further include an input unit, for example, the input unit 112 of FIG. 1 that receives a user's input for selecting the positioning mode of the X-ray apparatus.

The controller 2200 may supply power to, or may reduce or interrupt the power supplied to each X-ray detector so that the X-ray detector may operate in the determined power mode. Alternatively, the controller 2200 may control the communicator 2100 to transmit a signal indicating the determined power mode to each X-ray detector. Otherwise, the controller 2200 may transmit a signal indicating the determined power mode with respect to each X-ray detector, to the X-ray apparatus. The X-ray apparatus may control each X-ray detector to be operated in the determined power mode, based on the received signal.

When the non-usage times of the X-ray apparatus and the workstation 2000 exceed a threshold time, the controller 2200 may switch the operation modes of the X-ray apparatus and the workstation 2000 to the sleep mode. The controller 2200 may adaptively set the threshold time. The controller 2200 may set the threshold time in the method of adaptively setting the threshold time described with reference to FIG. 14. Accordingly, a description thereof will not be repeated here.

Also, since the controller 2200 corresponds to the controller 113 of FIG. 1, the description about the controller 113 in FIG. 1 may be applied to the controller 2200.

As such, the workstation 2000 according to the present exemplary embodiment may improve energy efficiency of the X-ray system including the X-ray apparatus and the workstation 2000.

Figure 18:
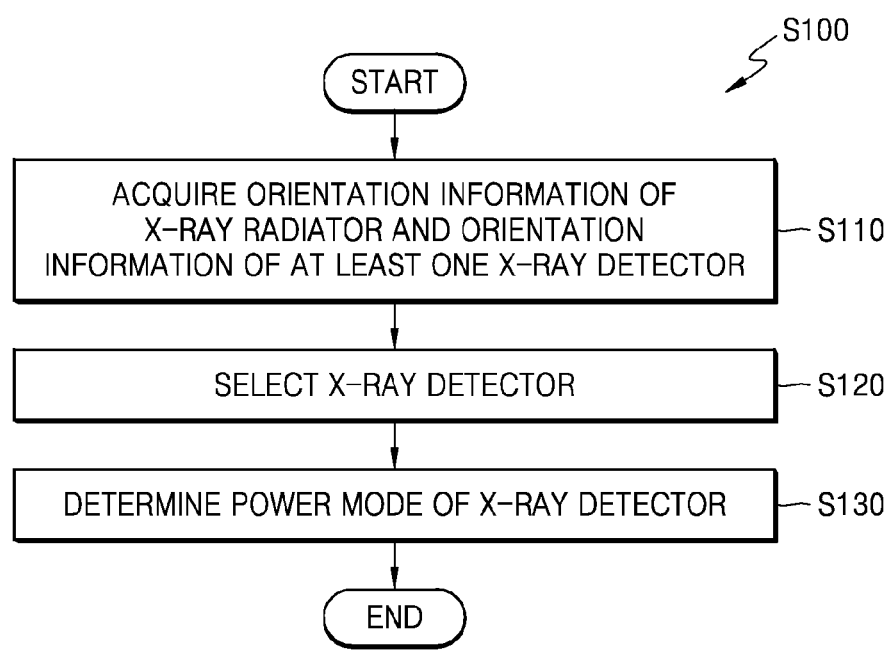
FIG. 18 is a flowchart of a method of operating an X-ray system according to an exemplary embodiment.

FIG. 18 is a flowchart of a method of operating an X-ray system according to an exemplary embodiment.

Referring to FIG. 18, the X-ray system may acquire orientation information of an X-ray radiator and orientation information of at least one X-ray detector (S110).

The X-ray system may select one of the at least one X-ray detector based on the orientation information of the X-ray radiator and the orientation information of the at least one X-ray detector (S120).

The X-ray system may determine the power mode of each X-ray detector (S130). The X-ray system may determine the power mode of the selected X-ray detector to be a power consumption mode. The X-ray system may determine the power mode of the X-ray detector that is not selected, to be a power save mode.

When any of the at least one X-ray detector is coupled to a receptor, the X-ray system may determine the power mode of the receptor to be the same as that of the X-ray detector coupled to the receptor.

The orientation information of the at least one X-ray detector may include information indicating whether the at least one X-ray detector is coupled to the receptor.

The X-ray system may acquire the orientation information of the X-ray radiator based on the positioning mode including the stand mode, the table mode, and the portable mode.

The X-ray system may receive a user's input for selecting the positioning mode.

The X-ray system may supply power or may interrupt the power supplied to each X-ray detector such that the X-ray detector is operated in the determined power mode. Alternatively, the X-ray system may transmit a signal indicating the determined power mode to each X-ray detector.

When a non-usage time of the X-ray system exceeds the threshold time, the X-ray system may switch the operation mode of the X-ray system to the sleep mode.

The method (S100) of operating the X-ray system of FIG. 18 may be performed by the above-described X-ray system, X-ray apparatus, or workstation. Each step of the method of operating an X-ray system may be performed by the above-described manner.

Figure 19:
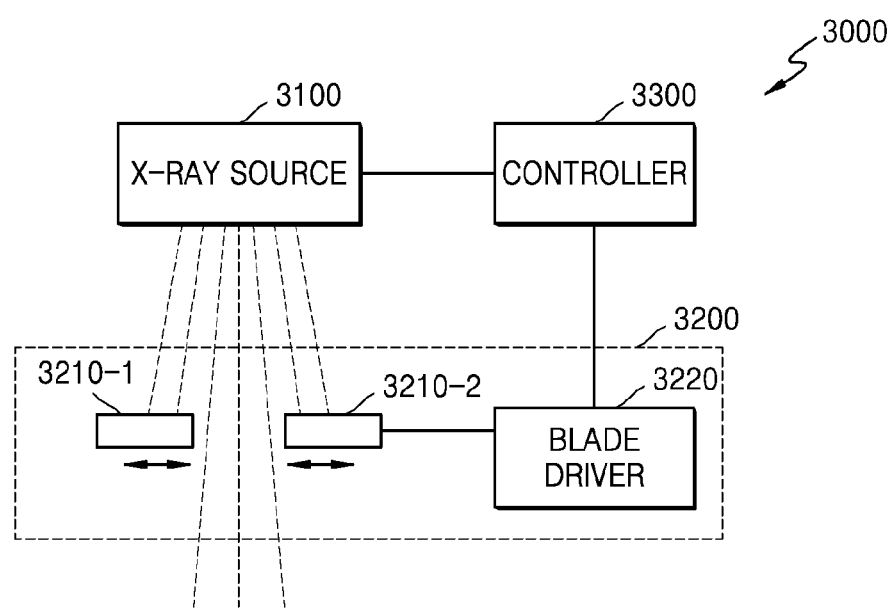
FIG. 19 illustrates an X-ray apparatus according to an exemplary embodiment.

FIG. 19 illustrates an X-ray apparatus 3000 according to an exemplary embodiment.

Referring to FIG. 19, the X-ray apparatus 3000 may include an X-ray source 3100, a collimator 3200, and a controller 3300. Although not illustrated in FIG. 19, the X-ray apparatus 3000 may further include other elements to be included in the above-described X-ray apparatus. Also, the above descriptions may be applied to the X-ray source 3100, the collimator 3200, and the controller 3300 without any separate descriptions.

The collimator 3200 may include blades 3210-1 and 3210-2 and a blade driver 3220. The blades 3210-1 and 3210-2 block an X-ray. Although FIG. 19 illustrates two blades 3210-1 and 3210-2, the number of blades included in the X-ray apparatus 3000 is not limited thereto and the collimator 3200 may include one blade or a plurality of blades.

The blade driver 3220 may move the blades 3210-1 and 3210-2. The blade driver 3220 may move the blades 3210-1 and 3210-2 respectively. When the X-ray apparatus 3000 includes a plurality of blades, the blade driver 3220 may include a plurality of drivers to move the respective blades. The blade driver 3220 may include a motor (not shown) and a motor driver (not shown) for driving the motor.

As the blades 3210-1 and 3210-2 are moved by the blade driver 3220, a region irradiated by an X-ray emitted by the X-ray source 3100 may be adjusted.

The controller 3300 may control an overall operation of the X-ray apparatus 3000. The controller 3300 may control the X-ray emission of the X-ray source 3100. The controller 3300 may adjust the X-ray irradiated region by controlling the blade driver 3220.

The controller 3300 may control the blade driver 3220 to move the blades 3210-1 and 3210-2 to the reference positions. The "reference positions" signify particular positions that may be references with respect to positions of the blades 3210-1 and 3210-2. For example, when the positions of the blades 3210-1 and 3210-2 at which the X-ray irradiated region is maximized or minimized may be the reference positions. However, the present disclosure is not limited thereto.

The controller 3300 may monitor the movements of the blades 3210-1 and 3210-2 after the blades 3210-1 and 3210-2 are moved to the reference positions. Accordingly, the controller 3300 may obtain relative positions that the blades 3210-1 and 3210-2 are moved from the reference positions. The "relative positions" may mean the amount of movements from the reference positions of the blades 3210-1 and 3210-2.

Figure 20:
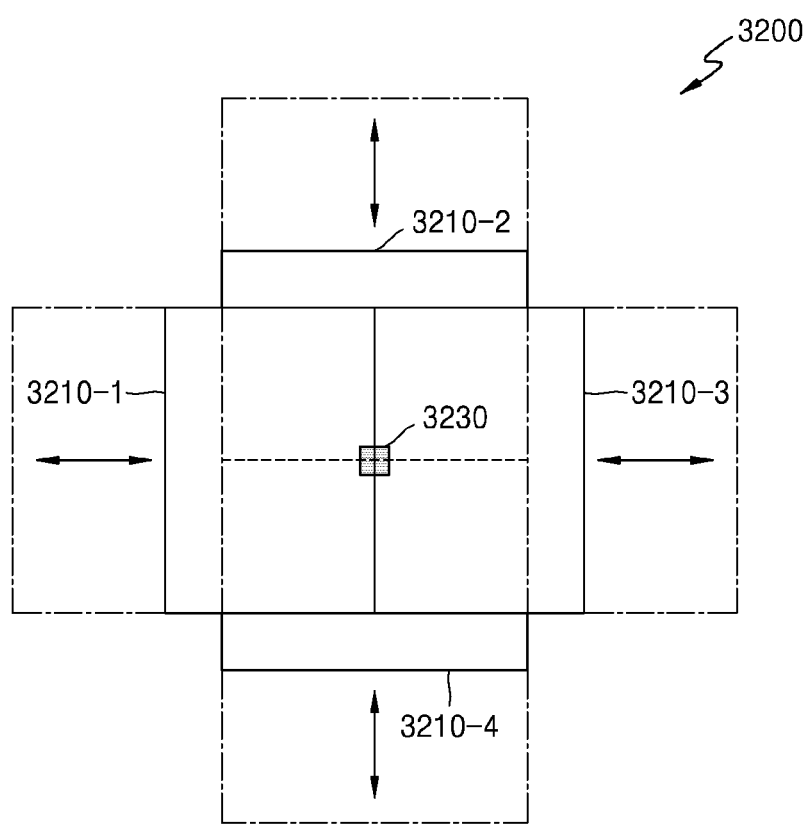
FIGS. 20 and 21 illustrate a process of obtaining the positions of blades by using the X-ray apparatus of FIG. 19.
Figure 21:
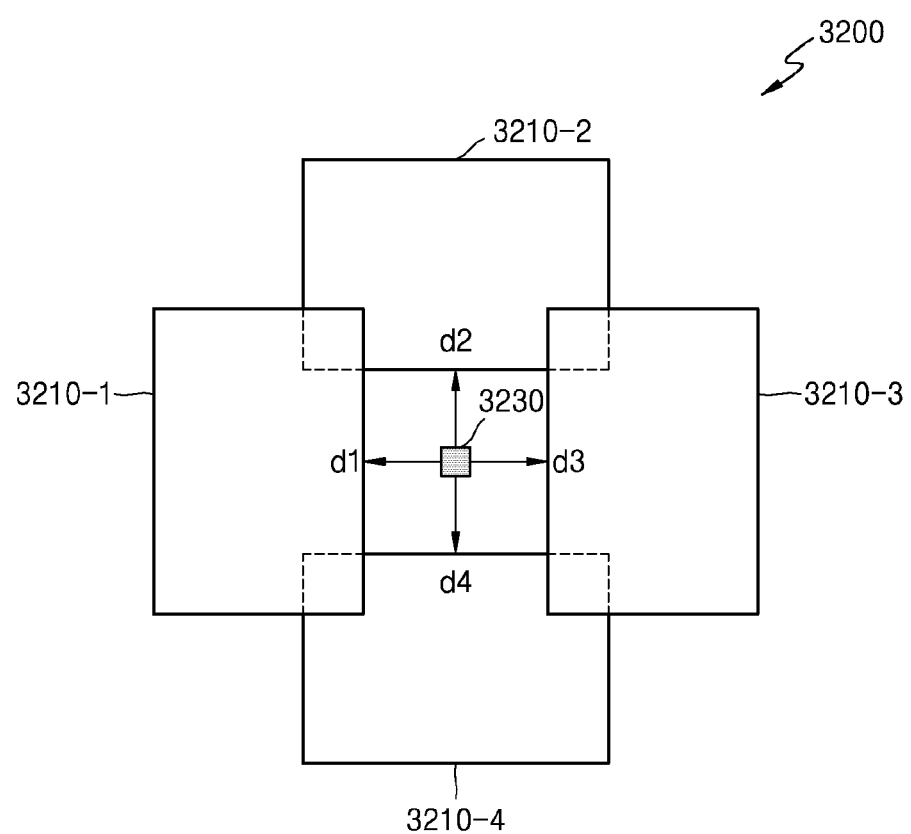

FIGS. 20 and 21 illustrate a process of obtaining the positions of blades by using the X-ray apparatus 3000 of FIG. 19. FIGS. 20 and 21 illustrate only the collimator 3200 included in the X-ray apparatus 3000 of FIG. 19.

Referring to FIG. 20, the collimator 3200 may include a plurality of blades 3210-1 to 3210-4 and a sensor 3230. Although FIG. 20 illustrates that the collimator 3200 includes four blades 3210-1 to 3210-4 and the shape of each of the blades 3210-1 to 3210-4 is rectangular, the number or shape of the blades included in the collimator 3200 of FIG. 20 are not limited thereto.

The sensor 3230 may be attached at a particular position in the collimator 3200 to sense that the blades 3210-1 to 3210-4 arrive at the reference positions. The sensor 3230 may be attached at the reference position.

In FIG. 20, when the blades 3210-1 to 3210-4 arrive at the reference positions, the X-ray irradiated region becomes minimized. In other words, the sensor 3230 may be attached at a position where the blades 3210-1 to 3210-4 that minimize the X-ray irradiated region are sensed. Although FIG. 20 illustrates that the sensor 3230 is attached at the center of the collimator 3200, the illustration of FIG. 20 is a mere example.

The controller 3300 may control the blade driver 3220 to move the blades 3210-1 to 3210-4 to the reference positions. The movements of the blades 3210-1 to 3210-4 to the reference positions may be referred to a blade reset. The blade reset may be performed when the power is first applied to the X-ray apparatus 3000.

When the blades 3210-1 to 3210-4 are moved to arrive at the reference positions, the sensor 3230 may transmit a signal indicating that the blades 3210-1 to 3210-4 are located at the reference positions, to the controller 3300. The signal may be an electrical signal, but the present disclosure is not limited thereto.

The sensor 3230 may sense in various ways that the blades 3210-1 to 3210-4 arrive at the reference positions. For example, the sensor 3230 may sense, by sensing light, whether the blades 3210-1 to 3210-4 arrive at the reference positions. In detail, when the blades 3210-1 to 3210-4 do not arrive at the reference positions, the sensor 3230 may sense light. When the blades 3210-1 to 3210-4 arrive at the reference positions, light is blocked so that the sensor 3230 may not sense light. However, this is a mere example and the sensor 3230 may sense in various ways whether the blades 3210-1 to 3210-4 arrive at the reference positions.

When receiving the signal from the sensor 3230, the controller 3300 recognizes that the blades 3210-1 to 3210-4 arrive at the reference positions. The controller 3300 may set the positions where the blades 3210-1 to 3210-4 are located at the time when the signal is received from the sensor 3230, to be the reference positions.

The controller 3300 may monitor the movements of the blades 3210-1 to 3210-4 from the time when the signal is received from the sensor 3230. The controller 3300 may obtain the relative positions that the blades 3210-1 to 3210-4 are moved from the reference positions.

The blades 3210-1 to 3210-4 located at the reference positions as illustrated in FIG. 20 may be moved to the positions as illustrated in FIG. 21.

Referring to FIG. 21, the blades 3210-1 to 3210-4 are moved from the reference positions by relative positions d1, d2, d3, and d4, respectively. The controller 3300 may obtain relative positions d1, d2, d3, and d4 that the blades 3210-1 to 3210-4 are moved from the reference positions by monitoring the movements of the blades 3210-1 to 3210-4 from the time when the signal is received from the sensor 3230. The controller 3300 may store the obtained relative positions d1, d2, d3, and d4 in a memory (not shown). The memory may be included in the X-ray apparatus 3000.

As illustrated in FIGS. 20 and 21, the controller 3300 may obtain the positions of the blades 3210-1 to 3210-4 by obtaining the relative positions d1, d2, d3, and d4 that the blades 3210-1 to 3210-4 are moved from the reference positions.

The X-ray apparatus 3000 according to the present exemplary embodiment may obtain the positions of the blades 3210-1 to 3210-4 without expensive equipment such as an absolute encoder capable of measuring the absolute position coordinates of the blades 3210-1 to 3210-4.

When the blades 3210-1 to 3210-4 are located at the positions as illustrated in FIG. 21, the power supplied to the collimator 3200 may be interrupted. The power interruption may occur for various reasons. For example, the power supplied to the collimator 3200 may be interrupted due to a blackout.

Also, when an operation mode of the X-ray apparatus 3000 is an off mode or a sleep mode, the power supplied to the collimator 3200 may be interrupted. For example, when the operation mode of the X-ray apparatus 3000 is switched from a use mode to a sleep mode, the power supplied to the collimator 3200 may be interrupted in a state in which the blades 3210-1 to 3210-4 are located as illustrated in FIG. 21.

The controller 3300 may control the blade driver 3220 to move the blades 3210-1 to 3210-4 to the reference positions at an initial stage of the use mode. The controller 3300 may obtain the relative positions to which the blades 3210-1 to 3210-4 are moved from the reference positions until the operation mode is switched from the use mode to the sleep mode. In other words, the controller 3300 may monitor the movements of the blades 3210-1 to 3210-4 while the operation mode is the use mode. The descriptions of FIGS. 13 and 14 may be applied to the case in which the operation mode of the X-ray apparatus 3000 is switched from the use mode to the sleep mode.

When the power supplied to the collimator 3200 is interrupted, the positions of the blades 3210-1 to 3210-4 may be changed by gravity, external impact, etc.

Figure 22:
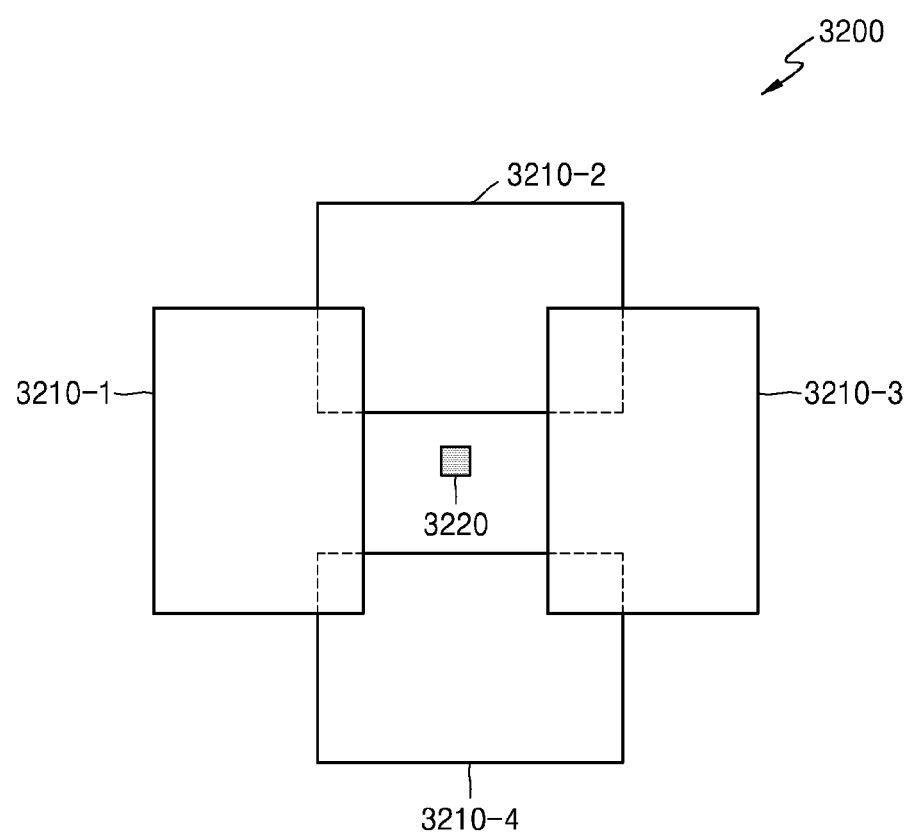
FIG. 22 illustrates an exemplary case in which of the positions of the blades located as illustrated in FIG. 21 are changed due to power interruption.

FIG. 22 illustrates an exemplary case in which of the positions of the blades located as illustrated in FIG. 21 are changed due to a power interruption.

Referring to FIG. 22, after the power interruption, the blades 3210-1 to 3210-4 may be freely moved. As illustrated in FIG. 22, when the blades 3210-1 to 3210-4 are moved to random positions and then power is resupplied, the X-ray apparatus 3000 may restore the blades 3210-1 to 3210-4 to a previous state before the power interruption as illustrated in FIG. 21. For example, when the operation mode is switched from the sleep mode to the use mode, power may be resupplied. However, it is a problem that the X-ray apparatus 3000 may not obtain current positions of the blades 3210-1 to 3210-4 without expensive equipment such as an absolute encoder capable of measuring the absolute position coordinates of the blades 3210-1 to 3210-4.

Figure 23A:
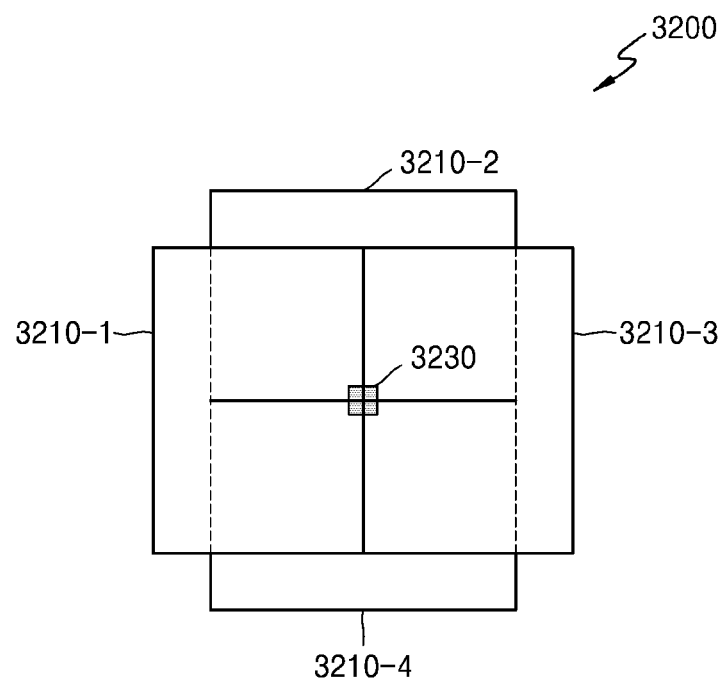
FIGS. 23A and 23B illustrate a process in which the X-ray apparatus restores the positions of the blades to a state before the power interruption.
Figure 23B:
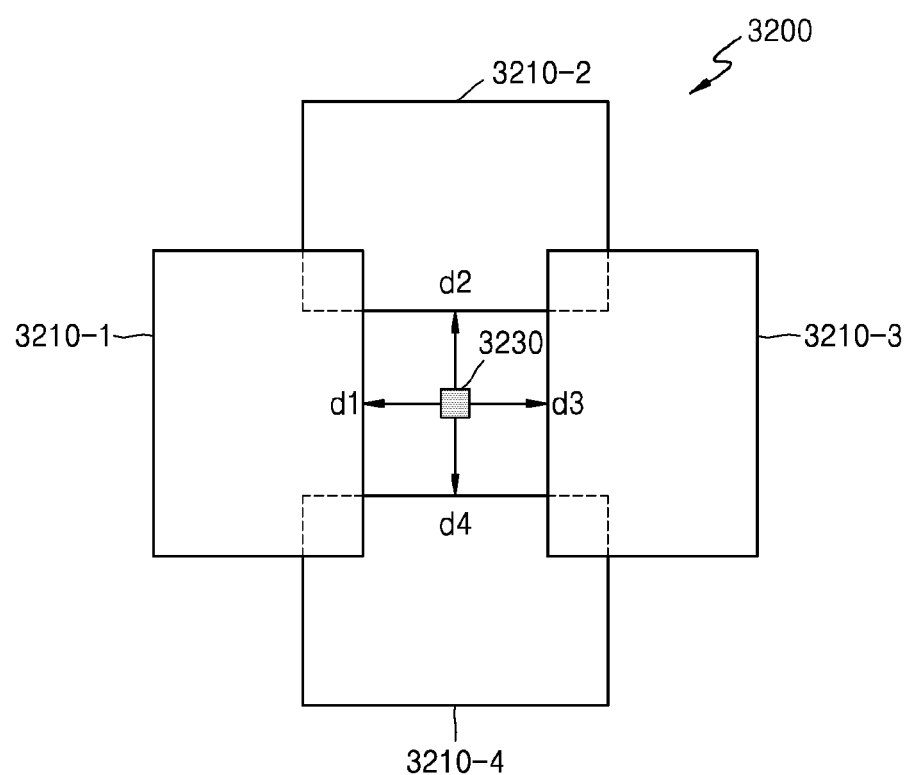

FIGS. 23A and 23B illustrate a process in which the X-ray apparatus 3000 restores the positions of the blades 3210-1 to 3210-4 to a state before the power interruption.

Referring to FIG. 23A, the controller 3300 may control the blade driver 3220 to move the blades 3210-1 to 3210-4 to the reference positions. When the blades 3210-1 to 3210-4 arrive at the reference position, the sensor 3230 may transmit a signal indicating that the blades 3210-1 to 3210-4 arrive at the reference positions, to the controller 3300.

Before the power interruption, in FIG. 21, the controller 3300 obtained the relative positions d1, d2, d3, and d4 of the blades 3210-1 to 3210-4 moved from the reference positions. Also, the obtained relative positions d1, d2, d3, and d4 may be stored in the memory.

The controller 3300 may control the blade driver 3220 to move the blades 3210-1 to 3210-4 located at the reference positions by the previously obtained relative positions d1, d2, d3, and d4. Accordingly, the blades 3210-1 to 3210-4 may be moved from FIG. 23A to FIG. 23B. FIG. 23B is the same as FIG. 21 that illustrates a state before the power interruption. In other words, the X-ray apparatus 3000 may restore the positions of the blades 3210-1 to 3210-4 to the same positions as before the power interruption.

As such, the X-ray apparatus 3000 according to the present exemplary embodiment may obtain the positions of the blades 3210-1 to 3210-4 without expensive equipment such as an absolute encoder capable of measuring the absolute position coordinates of the blades 3210-1 to 3210-4, by obtaining the relative positions d1, d2, d3, and d4 that the blades 3210-1 to 3210-4 with respect to the reference positions. Also, when the power is resupplied after the interruption, the blades 3210-1 to 3210-4 are restored to the reference positions and then moved by the previously obtained relative positions. Accordingly, the X-ray apparatus 3000 may restore the positions of the blades 3210-1 to 3210-4 to a state before the power interruption without expensive equipment such as an absolute encoder or a brake.

Since the positions of the blades 3210-1 to 3210-4 may be restored to a state before the power interruption without expensive equipment of a complicated process, when the X-ray apparatus 3000 is not used for a long time, the power supplied to the collimator 3200 is interrupted and thus a power efficiency of the X-ray apparatus 3000 may be improved. Accordingly, operating costs of the X-ray apparatus 3000 may be reduced.

Also, as a use environment of the collimator 3200 is maintained for an undesired change in the surrounding environment such as blackout or an external impact, robustness of the collimator 3200 may be improved. Also, since a user does not need to manipulate to restore the positions of the blades 3210-1 to 3210-4, user convenience may be improved.

When the positions of the blades 3210-1 to 3210-4 are restored to a state before the power interruption, the controller 3300 may monitor again the movement of the blades 3210-1 to 3210-4. In other words, the controller 3300 may obtain the relative positions of the blades 3210-1 to 3210-4 moved from the restored positions. The controller 3300 obtains the relative positions from the reference positions to the restored positions and the relative positions moved from the restored positions, and thus, may obtain the relative positions moved from the reference positions. In other words, the controller 3300 may continuously update the relative positions of the blades 3210-1 to 3210-4 from the reference positions.

Next, a method in which the controller 3300 obtains the relative positions d1, d2, d3, and d4 of the blades 3210-1 to 3210-4 moved from the reference positions is described below.

The blades 3210-1 to 3210-4 may be moved by the rotation of the motor included in the blade driver 3220 and the rotation direction and the number of turns of the motor may correspond to movement directions and degrees of movements of the blades 3210-1 to 3210-4. Accordingly, while the blades 3210-1 to 3210-4 are moved from the reference positions to the relative positions d1, d2, d3, and d4, the number of turns and the rotation directions of the motor included in the blade driver 3220 may correspond to the relative positions d1, d2, d3, and d4. The controller 3300 may continuously monitor the number of turns and the rotation direction of the motor to move the blades 3210-1 to 3210-4 after the blades 3210-1 to 3210-4 are moved to the reference positions. The controller 3300 may store the monitored number of turns and rotation direction of the motor in the memory. In order to obtain the number of turns and the rotation direction of the motor to move the blades 3210-1 to 3210-4, the controller 3300 may monitor the power supplied to the blade driver 3220 after the blades 3210-1 to 3210-4 are moved to the reference positions.

Figure 24:
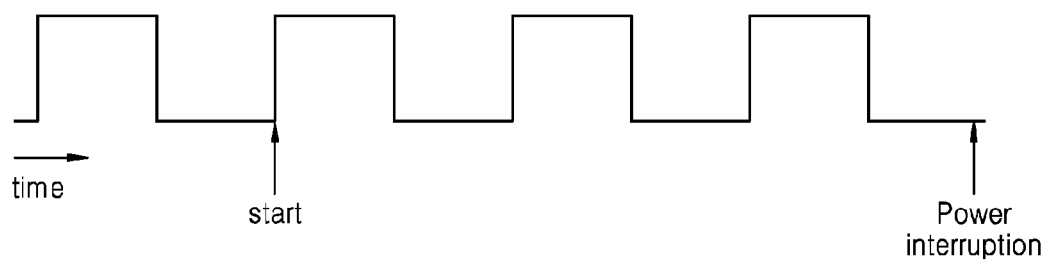
FIG. 24 illustrates an example of power supplied to a blade driver according to time.

FIG. 24 illustrates an example of power supplied to the blade driver 3220 according to time.

Referring to FIG. 24, the blade driver 3220 may receive pulse power according to time. For example, the motor included in the blade driver 3220 may be a step motor. The controller 3300 may monitor the number and positions of pulses that the blade driver 3220 receives from a start point when the blades 3210-1 to 3210-4 are moved to the reference positions to a time point when the power is interrupted. The start point may be a time point when the controller 3300 receives the signal from the sensor 3230.

Although FIG. 24 illustrates three pulses are supplied from a monitoring start point to the power interruption, this is a mere example for explanation. Since a pulse corresponds to a rotation angle of the motor, the number of pulses may correspond to the number of turns of the motor. In other words, the controller 3300 may obtain the relative positions of the blades 3210-1 to 3210-4 moved from the reference positions by monitoring the positions of pulses of the power that the blade driver 3220 receives from the time point when the blades 3210-1 to 3210-4 are moved to the reference positions to the power interruption.

In the above-described drawings, the reference positions are where the blades 3210-1 to 3210-4 minimize the X-ray irradiated region, and the sensor 3230 is located at the center of the collimator 3200. However, this is a mere example and other exemplary embodiments may be available.

Figure 25A:
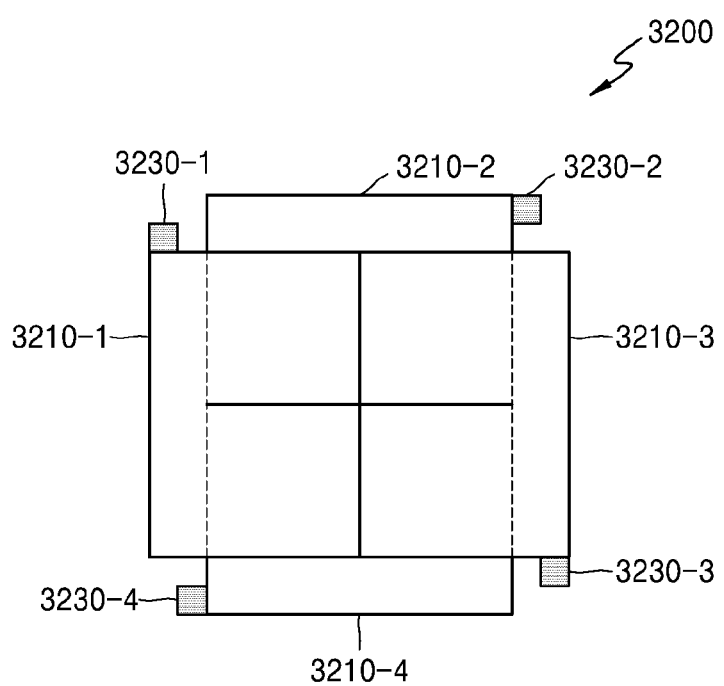
FIGS. 25A and 25B illustrate a case in which a plurality of sensors exist according to an exemplary embodiment.
Figure 25B:
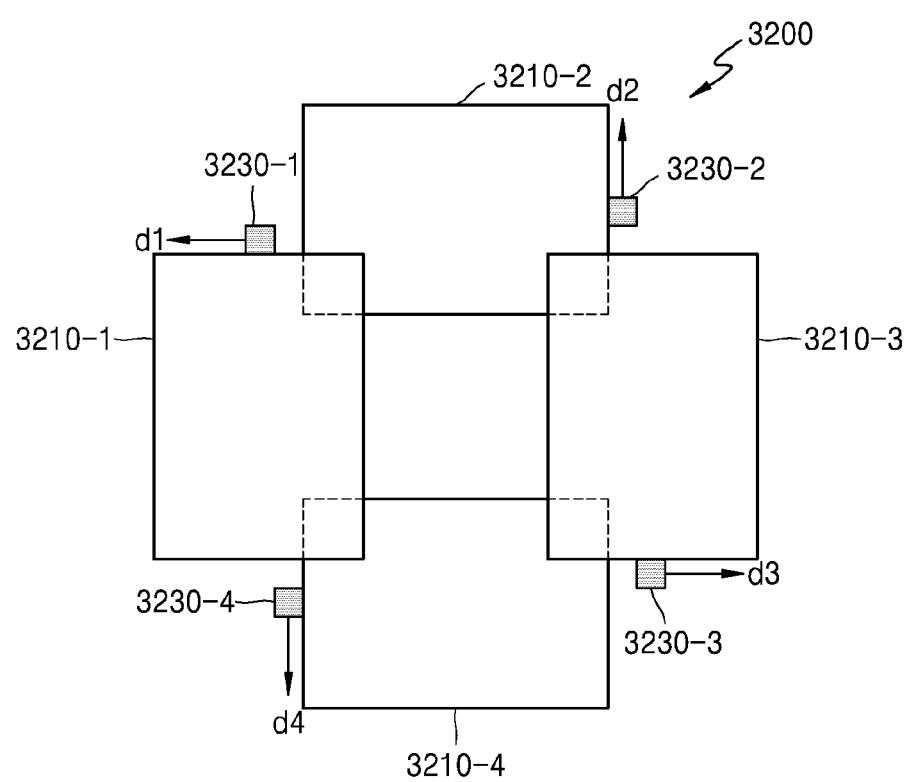

FIGS. 25A and 25B illustrate a case in which a plurality of sensors exist according to an exemplary embodiment.

Referring to FIG. 25A, each of a plurality of sensors 3230-1 to 3230-4 included in the collimator 3200 may be attached at a position where whether each of the blades 3210-1 to 3210-4 arrives at the reference position may be sensed. When the first blade 3210-1 arrives at the reference position, the first sensor 3230-1 may transmit a signal indicating the arrival to the controller 3300. When the second blade 3210-2 arrives at the reference position, the second sensor 3230-2 may transmit a signal indicating the arrival to the controller 3300. When the third blade 3210-3 arrives at the reference position, the third sensor 3230-3 may transmit a signal indicating the arrival to the controller 3300. When the fourth blade 3210-4 arrives at the reference position, the fourth sensor 3230-4 may transmit a signal indicating the arrival to the controller 3300.

After the blades 3210-1 to 3210-4 arrive at the reference positions as illustrated in FIG. 25A, the blades 3210-1 to 3210-4 may be moved as illustrated in FIG. 25B. The controller 3300 may obtain the relative positions d1, d2, d3, and d4 of the blades 3210-1 to 3210-4 moved from the reference positions.

The power may be interrupted when the blades 3210-1 to 3210-4 are located as illustrated in FIG. 25B. When the power is resupplied, the controller 3300 may control the blade driver 3220 to move the blades 3210-1 to 3210-4 to the reference positions. The controller 3300 may receive a signal indicating that the blades 3210-1 to 3210-4 arrive at the reference positions, from the first to fourth sensors 3230-1 to 3230-4. The controller 3300 may control the blade driver 3220 to move the blades 3210-1 to 3210-4 by the previously obtained relative positions d1, d2, d3, and d4. In other words, the X-ray apparatus 3000 may restore the blades 3210-1 to 3210-4 to the same positions as before the power interruption.

In FIGS. 25A and 25B, there are a plurality of sensors and the reference positions are where the blades 3210-1 to 3210-4 minimize the X-ray irradiated region. However, this is a mere example and an exemplary embodiment of FIG. 26 may be available.

Figure 26:
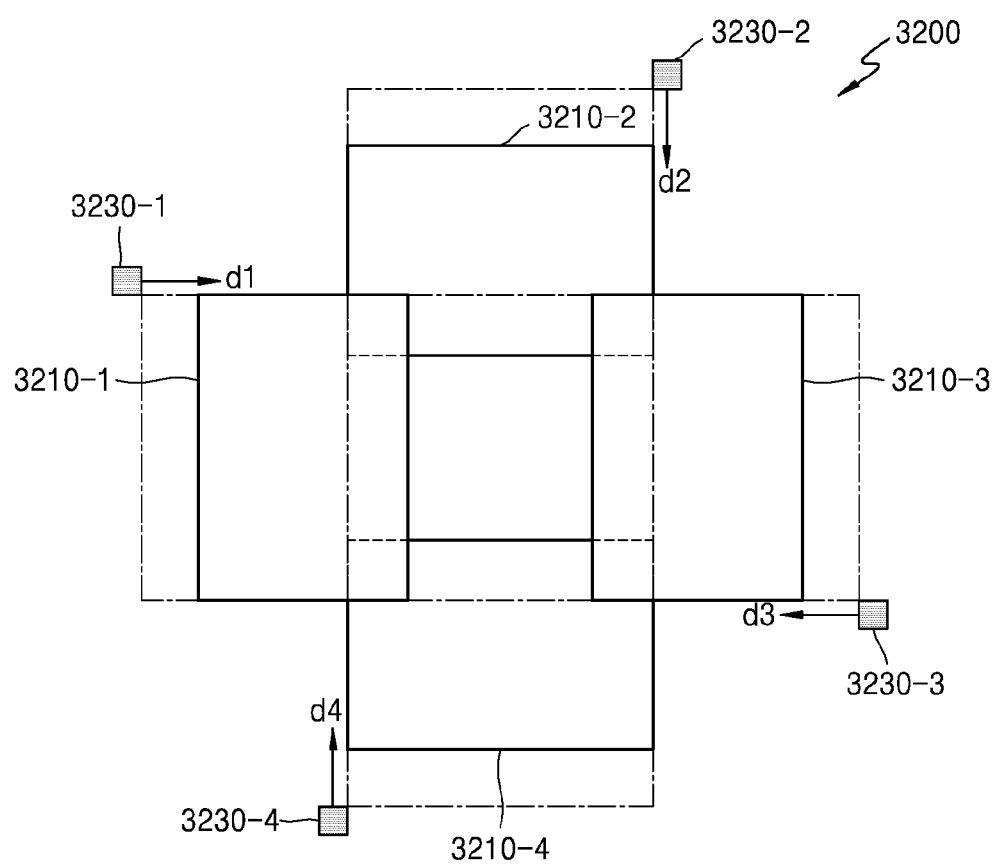
FIG. 26 illustrates a case in which a plurality of sensors exist according to an exemplary embodiment.

FIG. 26 illustrates a case in which a plurality of sensors exist according to an exemplary embodiment.

Referring to FIG. 26, the first to fourth sensors 3230-1 to 3230-4 included in the collimator 3200 are attached at places to sense positions where the blades 3210-1 to 3210-4 maximize the X-ray irradiated region. In other words, the reference positions in FIG. 26 are where the blades 3210-1 to 3210-4 maximize the X-ray irradiated region.

The controller 3300 may perform the process of obtaining the positions of the blades 3210-1 to 3210-4 as follows.

The controller 3300 may control the blade driver 3220 to move the blades 3210-1 to 3210-4 to the reference positions where the X-ray irradiated region is maximized. When the blades 3210-1 to 3210-4 arrive at the reference positions, the first to fourth sensors 3230-1 to 3230-4 transmit signals indicating that the blades 3210-1 to 3210-4 arrive at the reference positions, to the controller 3300.

The controller 3300 may obtain the relative positions d1, d2, d3, and d4 of the blades 3210-1 to 3210-4 moved from the reference positions after the signal is received. The controller 3300 may store the relative positions d1, d2, d3, and d4 from the obtained reference positions in the memory.

When the power supplied to the collimator 3200 is resupplied after the interruption, the controller 3300 may perform the restoration process of the positions of the blades 3210-1 to 3210-4 as follows.

The controller 3300 may control the blade driver 3220 to move the blades 3210-1 to 3210-4 to the reference positions where the X-ray irradiated region is maximized. When the blades 3210-1 to 3210-4 arrive at the reference positions, the first to fourth sensors 3230-1 to 3230-4 transmit signals indicating that the blades 3210-1 to 3210-4 arrive at the reference positions, to the controller 3300.

The controller 3300 may control the blade driver 3220 to move the blades 3210-1 to 3210-4 by the previously obtained relative positions d1, d2, d3, and d4 from the reference positions. In other words, the X-ray apparatus 3000 may restore the blades 3210-1 to 3210-4 to the same positions as before the power interruption.

Figure 27:
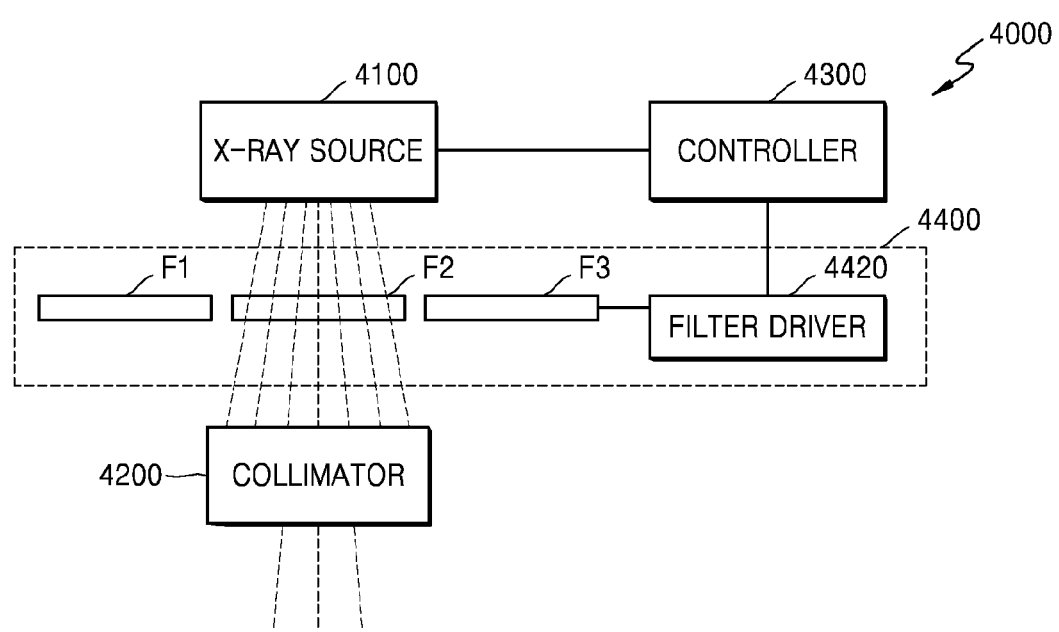
FIG. 27 illustrates an X-ray apparatus according to an exemplary embodiment.

FIG. 27 illustrates an X-ray apparatus 4000 according to an exemplary embodiment.

Referring to FIG. 27, the X-ray apparatus 4000 may include an X-ray source 4100, a collimator 4200, a controller 4300, and a filter unit 4400. Although not illustrated in FIG. 27, the X-ray apparatus 4000 may further include other constituent elements included in the above-described X-ray apparatus. Also, the above descriptions may be applied to the X-ray source 4100, the collimator 4200, and the controller 4300 without further reference thereto. Although FIG. 27 illustrates the filter unit 4400 to be separated from the collimator 4200, the filter unit 4400 may be included in the collimator 4200.

The filter unit 4400 may include a plurality of filters F1, F2, and F3 and a filter driver 4420. The filters F1, F2, and F3 may filter an X-ray, and the filters F1, F2, and F3 may have different filtering energy bands. Also, doses of a filtered X-ray are different according to the filters F1, F2, and F3. Although FIG. 27 illustrates three filters F1, F2, and F3, the number of filters included in the filter unit 4400 of FIG. 27 is not limited thereto.

The filter driver 4420 may move the filters F1, F2, and F3. In FIG. 27, the second filter F2 of the filters F1, F2, and F3 may be located under the X-ray source 4100 to filter an X-ray emitted from the X-ray source 4100. As the filter driver 4420 moves the filters F1, F2, and F3, other filter F1 or F3 may be located under the X-ray source 4100. The filter driver 4420 may include a motor (not shown) and a motor driver (not shown) for driving the motor.

The controller 4300 may control an overall operation of the X-ray apparatus 4000. The controller 4300 may control the X-ray emission of the X-ray source 4100. The controller 4300 may control the filter driver 4420 such that one of the filters F1, F2, and F3 filters the X-ray emitted from the X-ray source 4100.

The controller 4300 may control the filter driver 4420 to move the filters F1, F2, and F3 to the reference positions. The "reference positions" signify particular positions that may be references with respect to positions of the filters F1, F2, and F3. For example, the positions of the filters F1, F2, and F3 when a particular one of the filters F1, F2, and F3 is located under the X-ray source 4100 may be the reference positions. However, the present disclosure is not limited thereto. The "relative positions" may mean the amount of movements from the reference positions of the filters F1, F2, and F3.

The controller 4300 may monitor the movements of the filters F1, F2, and F3 after the filters F1, F2, and F3 are moved to the reference positions. Accordingly, the controller 4300 may obtain the relative positions of the filters F1, F2, and F3 moved from the reference positions.

Figure 28:
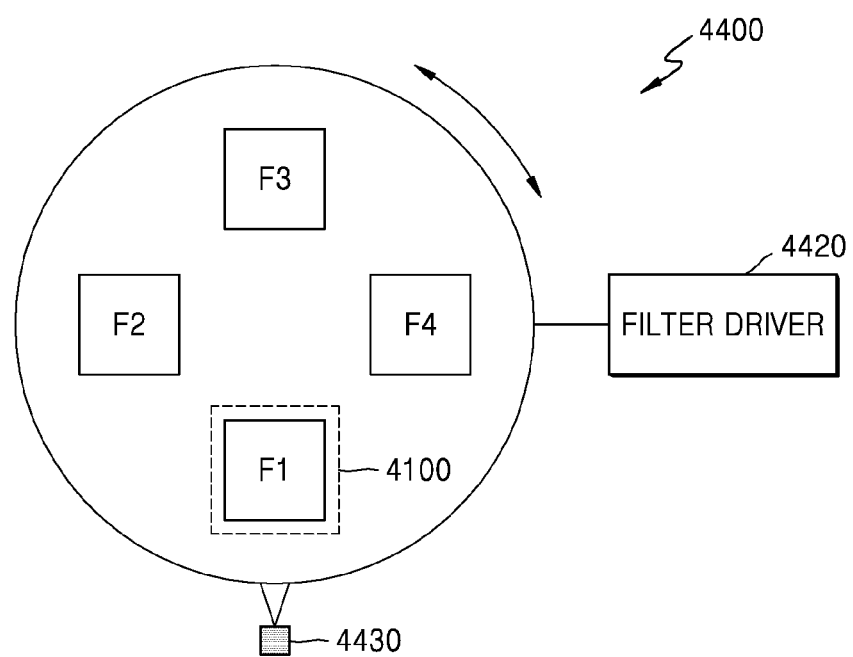
FIGS. 28 and 29 illustrate a process in which the X-ray apparatus of FIG. 27 obtains positions of a plurality of filters.
Figure 29:
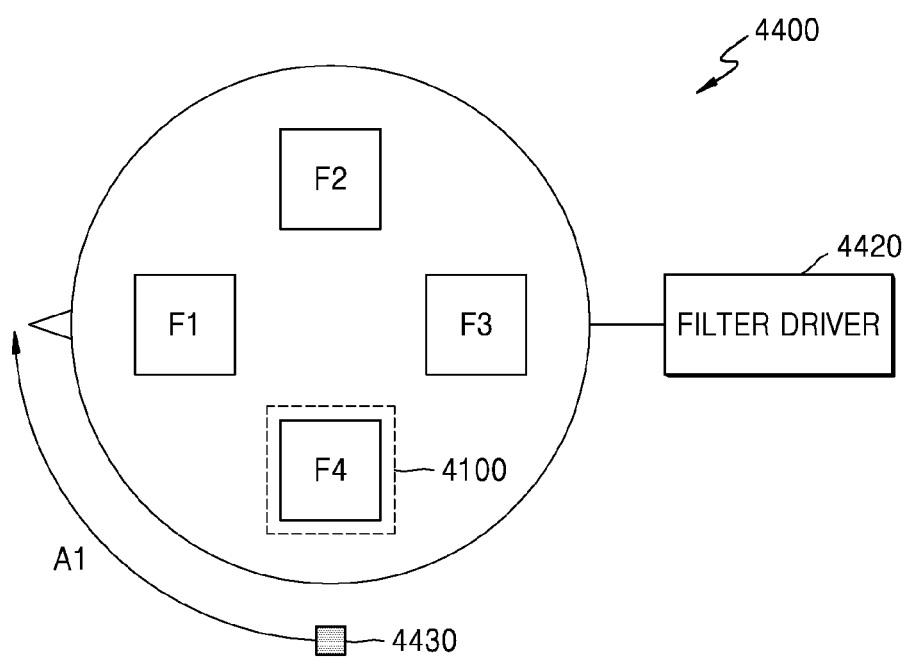

FIGS. 28 and 29 illustrate a process in which the X-ray apparatus 4000 of FIG. 27 obtains the positions of the filters F1, F2, and F3.

Referring to FIG. 28, the filter unit 4400 may include a plurality of filters F1 to F4, the filter driver 4420, and a sensor 4430. Although FIG. 28 illustrates that the filter unit 4400 includes four filters F1 to F4 and the filters F1 to F4 are arranged on a disc, the number or shape of the filters included in the filter unit 4400 of FIG. 28 is not limited thereto.

As the filter driver 4420 rotates the filters F1 to F4, the positions of the filters F1 to F4 may be changed. Although FIG. 28 illustrates that the first filter F1 is located under the X-ray source 4100, as the filter driver 4420 rotates the filters F1 to F4, another filter may be located under the X-ray source 4100.

The sensor 4430 may be attached at a particular position where whether the filters F1 to F4 arrive at the reference positions in the filter unit 4400 is sensed.

In FIG. 28, when the filters F1 to F4 arrive at the reference positions, the first filter F1 is located under the X-ray source 4100. In other words, the sensor 4430 may be attached a position where whether the first filter F1 is located under the X-ray source 4100 is sensed. In FIG. 28, the position of the sensor 4430 is a mere example.

The controller 4300 may control the filter driver 4420 to move the filters F1 to F4 to the reference positions. The movements of the filters F1 to F4 to the reference positions may be referred to as the filter reset. The filter reset may be performed when power is first applied to the X-ray apparatus 4000.

When the filters F1 to F4 are moved to arrive at the reference positions, the sensor 4430 may transmit a signal indicating that the filters F1 to F4 are located at the reference positions, to the controller 4300. The signal may be an electrical signal, but the present disclosure is not limited thereto.

The sensor 4430 may sense in various ways that the filters F1 to F4 arrive at the reference positions. Although in FIG. 28 the sensor 4430 may sense by touch whether the filters F1 to F4 arrive at the reference positions, the present disclosure is not limited thereto.

When receiving the signal from the sensor 4430, the controller 4300 recognizes that the filters F1 to F4 arrive at the reference positions. The controller 4300 may set the positions where the filters F1 to F4 are located at the time when the signal is received from the sensor 4430, to be the reference positions.

The controller 4300 may monitor the movements of the filters F1 to F4 from the time when the signal is received from the sensor 4430. The controller 4300 may obtain the relative positions that the filters F1 to F4 are moved from the reference positions.

The filters F1 to F4 located at the reference positions as illustrated in FIG. 28 may be moved to the positions as illustrated in FIG. 29.

Referring to FIG. 29, the filters F1 to F4 are moved by a position A1 from the reference positions. The filter located under the X-ray source 4100 is changed from the first filter F1 to the fourth filter F4.

The controller 4300 may obtain the relative position A1 that the filters F1 to F4 are moved from the reference positions by monitoring the movements of the filters F1 to F4 from the time when the signal is received from the sensor 4430. The controller 4300 may store the obtained relative position A1 in a memory (not shown). The memory may be included in the X-ray apparatus 4000.

In order to obtain the relative position A1 that the filters F1 to F4 are moved from the reference positions, the controller 4300 may continuously monitor the number of turns and the rotation direction of the motor included in the filter driver 4420 that moves the filters F1 to F4, after the filters F1 to F4 are moved to the reference positions. Alternatively, the controller 4300 may monitor the number and positions of pulses that the filter driver 4420 receives, from the time when the filters F1 to F4 are moved to the reference positions to a time point when the power is interrupted.

As illustrated in FIGS. 28 and 29, the controller 4300 may obtain the positions of the filters F1 to F4 by obtaining the relative position A1 that the filters F1 to F4 are moved from the reference positions.

The X-ray apparatus 4000 according to the present exemplary embodiment may obtain the positions of the filters F1 to F4 without expensive equipment such as an absolute encoder capable of measuring the absolute position coordinates of the filters F1 to F4.

When the filters F1 to F4 are located at the positions as illustrated in FIG. 29, the power supplied to the filter driver 4420 may be interrupted. The power interruption may occur for various reasons. For example, the power supplied to the filter driver 4420 may be interrupted due to a blackout.

Also, when an operation mode of the X-ray apparatus 4000 is an off mode or a sleep mode, the power supplied to the filter driver 4420 may be interrupted. For example, when the operation mode of the X-ray apparatus 4000 is switched from a use mode to a sleep mode, the power supplied to the filter driver 4420 may be interrupted in a state in which the filters F1 to F4 are located as illustrated in FIG. 29.

The controller 4300 may control the filter driver 4420 to move the filters F1 to F4 to the reference positions at an initial stage of the use mode. The controller 4300 may obtain the relative positions to which the filters F1 to F4 are moved from the reference positions until the operation mode is switched from the use mode to the sleep mode. In other words, the controller 4300 may monitor the movements of the filters F1 to F4 while the operation mode is the use mode. The descriptions of FIGS. 13 and 14 may be applied to the case in which the operation mode of the X-ray apparatus 4000 is switched from the use mode to the sleep mode.

When the power supplied to the filter driver 4420 is interrupted, the positions of the filters F1 to F4 may be changed by gravity, external impact, etc.

Figure 30:
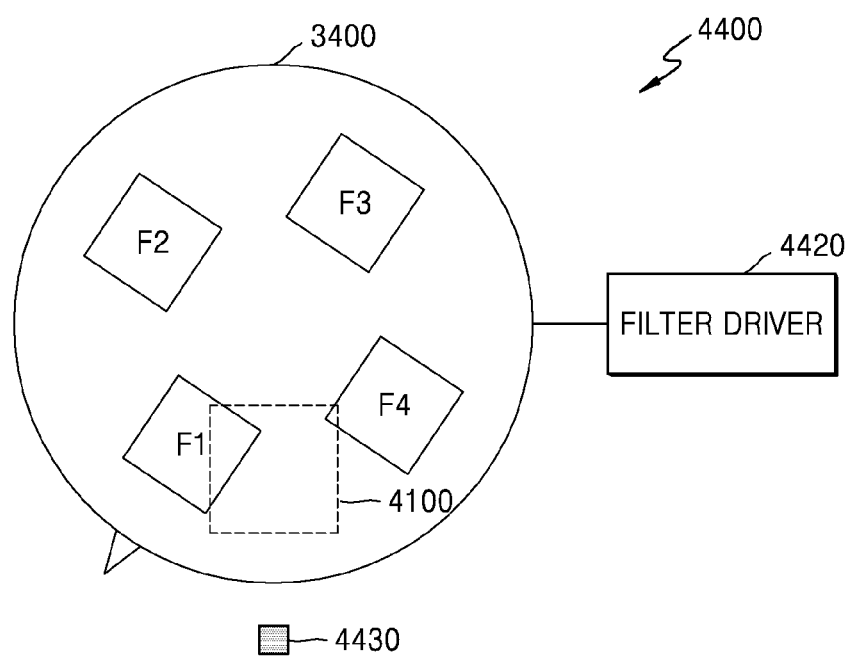
FIG. 30 illustrates a case in which the positions of the filters located as shown in FIG. 29 are changed due to power interruption.

FIG. 30 illustrates a case in which the positions of the filters F1 to F4 located as shown in FIG. 29 are changed due to power interruption.

Referring to FIG. 30, after the power interruption, the filters F1 to F4 may be freely moved. As illustrated in FIG. 30, when the filters F1 to F4 are moved to random positions and then power is resupplied, the X-ray apparatus 4000 may restore the filters F1 to F4 to the positions of FIG. 29 that is a previous state before the power interruption. However, it is a problem that the X-ray apparatus 4000 may not obtain current positions of the filters F1 to F4 without expensive equipment such as an absolute encoder capable of measuring the absolute position coordinates of the filters F1 to F4.

Figure 31A:
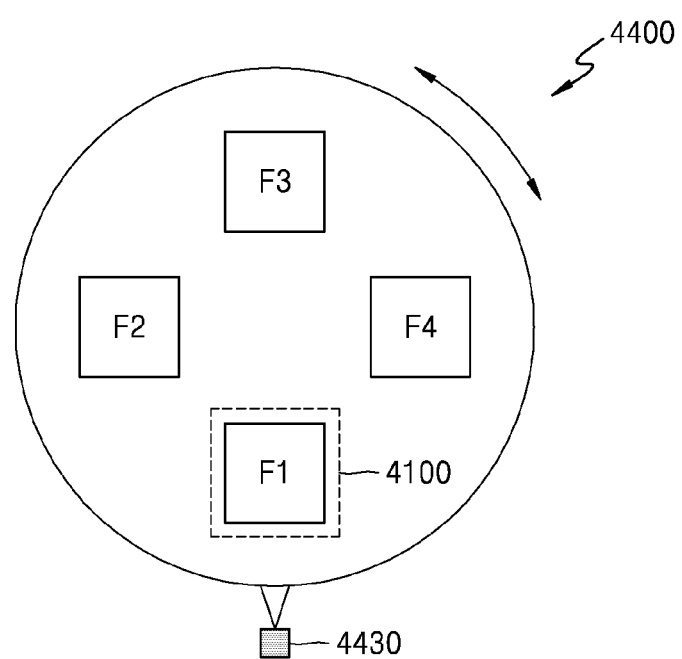
FIGS. 31A and 31B illustrate a process in which the X-ray apparatus restores the positions of the filters to a state before the power interruption.
Figure 31B:
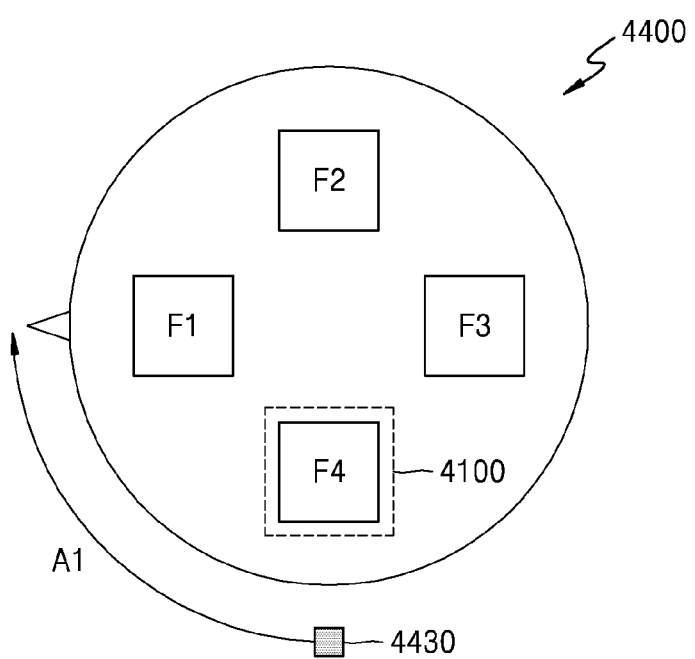

FIGS. 31A and 31B illustrate a process in which the X-ray apparatus 4000 restores the positions of the filters to a state before the power interruption.

Referring to FIG. 31A, the controller 4300 may control the filter driver 4420 to move the filters F1 to F4 to the reference positions. When the filters F1 to F4 are moved to arrive at the reference positions, the sensor 4430 may transmit a signal indicating that the filters F1 to F4 arrive at the reference positions, to the controller 4300.

Before power is interrupted, in FIG. 29, the controller 4300 obtains the relative position A1 that the filters F1 to F4 are moved from the reference positions. Also, the obtained relative position A1 may be stored in the memory.

The controller 4300 may control the filter driver 4420 to move the filters F1 to F4 located at the reference positions by the relative position A1 that is previously obtained.

Accordingly, the filters F1 to F4 are moved from FIG. 31A to FIG. 31B. FIG. 31B is the same as FIG. 29 that illustrates a state before the power interruption. In other words, the X-ray apparatus 4000 may restore the positions of the filters F1 to F4 to the same positions as before the power interruption.

When the positions of the filters F1 to F4 are restored to a state before the power interruption, the controller 4300 may monitor again the movements of the filters F1 to F4. In other words, the controller 4300 may obtain the relative positions of the filters F1 to F4 moved from the restored positions. The controller 4300 obtains the relative positions from the reference positions to the restored positions and the relative positions moved from the restored positions, and thus, may obtain the relative positions moved from the reference positions. In other words, the controller 4300 may continuously update the relative positions of the filters F1 to F4 from the reference positions.

As such, the X-ray apparatus 4000 according to the present exemplary embodiment may obtain the positions of the filters F1 to F4 without expensive equipment capable of measuring the absolute position coordinates of the filters F1 to F4, by obtaining the relative positions of the filters F1 to F4 with respect to the reference position. Also, when the power is resupplied after the interruption, the filters F1 to F4 are moved back to the reference positions and then moved by the previously obtained relative positions. Accordingly, the X-ray apparatus 4000 may restore the positions of the filters F1 to F4 to a state before the power interruption without expensive equipment such as an absolute encoder or a brake.

Since the positions of the filters F1 to F4 may be restored to a state before the power interruption without expensive equipment of a complicated process, when the X-ray apparatus 4000 is not used for a long time, the power supplied to the filter unit 4400 is interrupted and thus a power efficiency of the X-ray apparatus 4000 may be improved. Accordingly, operating costs of the X-ray apparatus 4000 may be reduced.

Also, as a use environment of the filter driver 4420 is maintained for an undesired change in the surrounding environment such as blackout or an external impact, robustness of the filter unit 4400 may be improved. Also, since a user does not need to manipulate the X-ray apparatus 4000 to restore the positions of the filters F1 to F4, user convenience may be improved.

Figure 32:
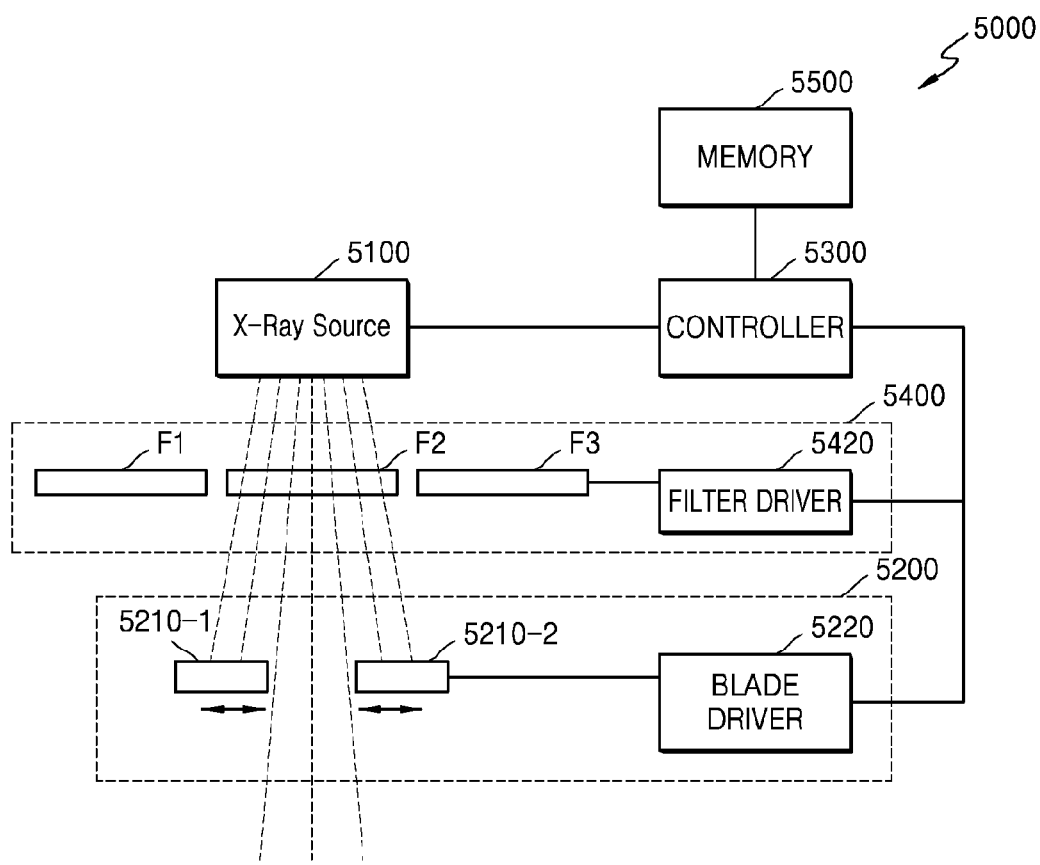
FIG. 32 illustrates an X-ray apparatus according to an exemplary embodiment.

FIG. 32 illustrates an X-ray apparatus 5000 according to an exemplary embodiment.

Referring to FIG. 32, the X-ray apparatus 5000 may include an X-ray source 5100, a collimator 5200, a controller 5300, a filter unit 5400, and a memory 5500. Although not illustrated in FIG. 32, the X-ray apparatus 5000 may further include other constituent elements included in the above-described X-ray apparatus. Although FIG. 32 illustrates the filter unit 5400 to be separated from the collimator 5200, the filter unit 5400 may be included in the collimator 5200.

The collimator 5200 may include blades 5210-1 and 5210-2 and a blade driver 5220. Alternatively, the collimator 5200 may include only one blade. The filter unit 5400 may include filters F1, F2, and F3, and a filter driver 5420.

The controller 5300 may control the blade driver 5220 to move the blades 5210-1 and 5210-2 to first reference positions. The controller 5300 may control the filter driver 5420 to move the filters F1, F2, and F3 to second reference positions.

The controller 5300 may obtain relative positions of the blades 5210-1 and 5210-2 moved from the first reference positions. The controller 5300 may obtain relative positions of the filters F1, F2, and F3 moved from the second reference positions.

The controller 5300 may store the obtained relative positions from the first and second reference positions in the memory 5500.

When power is resupplied after the interruption, the controller 5300 may control the blade driver 5220 and the filter driver 5420 to move the blades 5210-1 and 5210-2 and the filters F1, F2, and F3 to the first and second reference positions, respectively. Next, the controller 5300 controls the blade driver 5220 and the filter driver 5420 using the relative positions stored in the memory 5500, to restore the blades 5210-1 and 5210-2 and the filters F1, F2, and F3 to the same positions as before the power interruption.

The above-described methods of obtaining and restoring the positions of the blades or filters may be performed by the workstation 110 of FIG. 1 or 2000 of FIG. 17 for controlling an X-ray apparatus. The controller 113 of FIG. 1 or 2200 of FIG. 17 of the workstation 110 of FIG. 1 or 2000 of FIG. 17 may control the blade driver 5220 to move the blades 5210-1 and 5210-2 to the first reference positions, and obtain the first relative positions of the blades 5210-1 and 5210-2 moved from the first reference positions. Also, the controller 113 of FIG. 1 or 2200 of FIG. 17 of the workstation 110 of FIG. 1 or 2000 of FIG. 17 may control the filter driver 5420 to move the filters F1, F2, and F3 to the second reference positions, and obtain the second relative positions of the filters F1, F2, and F3 moved from the second reference positions.

When the power supplied to the X-ray apparatus 5000 is interrupted and then resupplied, the controller 113 of FIG. 1 or 2200 of FIG. 17 of the workstation 110 of FIG. 1 or 2000 of FIG. 17 may control the blade driver 5220 to move the blades 5210-1 and 5210-2 to the first reference positions and then from the first reference positions by the first relative positions.

When the power supplied to the X-ray apparatus 5000 is interrupted and then resupplied, the controller 113 of FIG. 1 or 2200 of FIG. 17 of the workstation 110 of FIG. 1 or 2000 of FIG. 17 may control the filter driver 5420 to move the filters F1, F2, and F3 to the second reference positions and then from the second reference positions by the second relative positions.

As such, the controller 113 of FIG. 1 or 2200 of FIG. 17 of the workstation 110 of FIG. 1 or 2000 of FIG. 17 may obtain the positions of the blades 5210-1 and 5210-2 and the positions of the filters F1, F2, and F3 by controlling the blade driver 5220 and the filter driver 5420 included in the X-ray apparatus 5000. Also, the controller 113 of FIG. 1 or 2200 of FIG. 17 of the workstation 110 of FIG. 1 or 2000 of FIG. 17 may restore the positions of the blades 5210-1 and 5210-2 and the positions of the filters F1, F2, and F3 to states before the power interruption. Also, the above-described operations performed in the X-ray apparatus 5000 in relation with the obtaining and restoring of the positions of the blades 5210-1 and 5210-2 and the filters F1, F2, and F3 may be performed in the workstation 110 of FIG. 1 or 2000 of FIG. 17.

Figure 33:
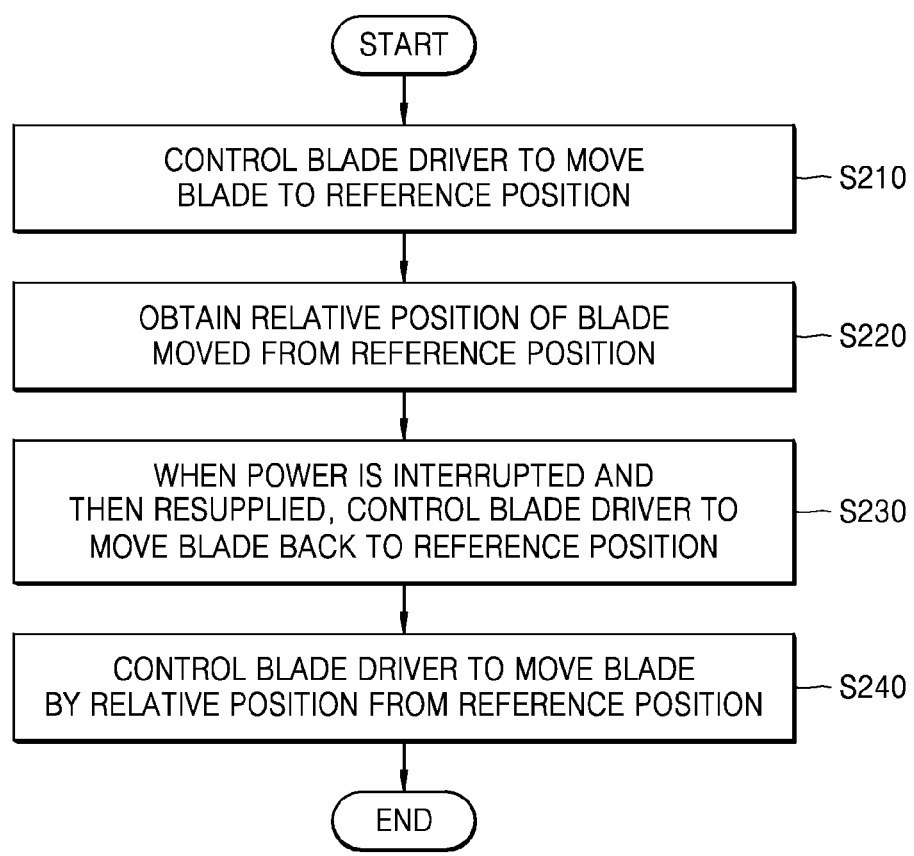
FIG. 33 is a flowchart of a method of operating an X-ray system according to an exemplary embodiment.

FIG. 33 is a flowchart of a method of operating an X-ray system according to an exemplary embodiment.

Referring to FIG. 33, the X-ray system may control a blade driver to move a blade for blocking an X-ray to a reference position (S210). The X-ray system may obtain a relative position of the blade moved from the reference position (S220). As such, the X-ray system may obtain a position of the blade.

When power is resupplied after interruption, the X-ray system may control the blade driver to move the blade back to the reference position (S230). The X-ray system may control the blade driver such that the blade is moved from the reference position by a relative position (S240). Accordingly, the X-ray system may restore the position of the blade to a state before the power interruption.

Figure 34:
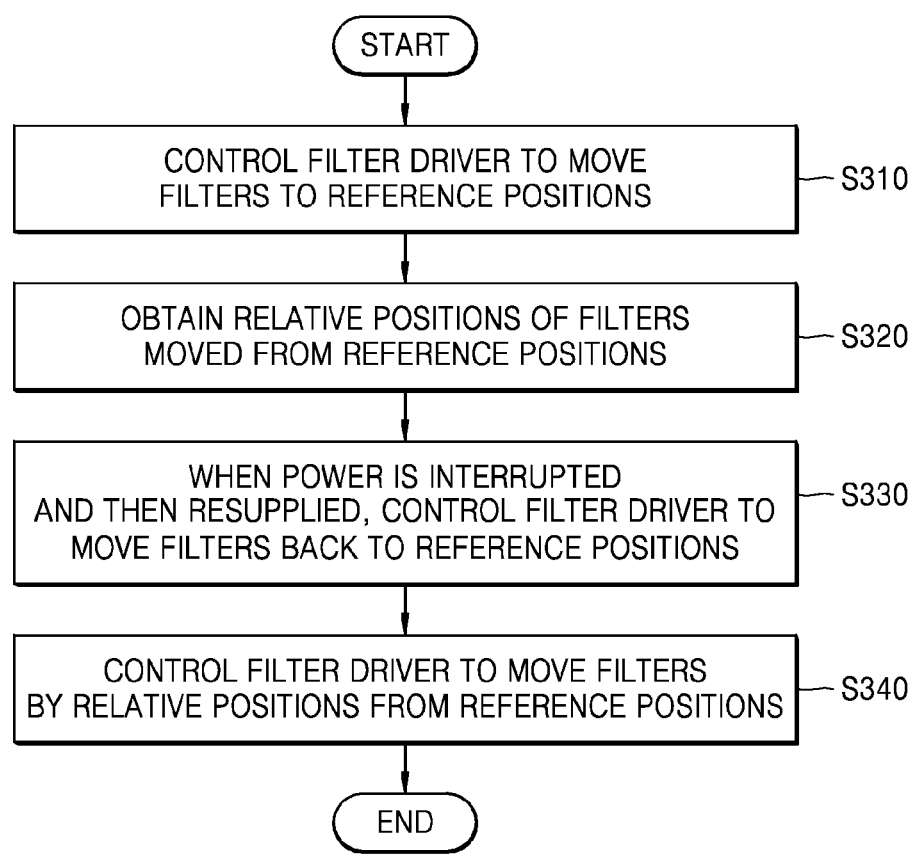
FIG. 34 is a flowchart of a method of operating an X-ray system according to an exemplary embodiment.

FIG. 34 is a flowchart of a method of operating an X-ray system according to an exemplary embodiment.

Referring to FIG. 34, the X-ray system may control a filter driver to move a plurality of filters for filtering an X-ray to a reference position (S310). The X-ray system may obtain relative positions of the filters moved from the reference position (S320). As such, the X-ray system may obtain positions of the filters.

When power is resupplied after interruption, the X-ray system may control the filter driver to move the filters back to the reference position (S330). The X-ray system may control the filter driver such that the filters are moved from the reference position by relative positions (S340). Accordingly, the X-ray system may restore the positions of the filters to a state before the power interruption.

The operation methods of the X-ray system described in FIGS. 33 and 34 may be performed in the X-ray system, the X-ray apparatus, and the workstation of the above-described drawings. All descriptions presented before FIGS. 33 and 34 may be applied to the operation method of the X-ray system.

In addition, other exemplary embodiments of the present inventive concept can also be implemented through computer readable code/instructions in/on a medium, e.g., a computer readable medium, to control at least one processing element to implement any of the above described exemplary embodiments. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments of the present inventive concept have been described with reference to the figures, it will be understood by those of ordinary skill in the art that various changes in form and details may be made therein without departing from the spirit and scope of the present inventive concept as defined by the following claims.

What is claimed is:
1. An X-ray apparatus comprising:
an X-ray radiator configured to radiate an X-ray; and
a controller configured to:
acquire orientation information of the X-ray radiator including information indicating an X-ray radiation direction of the X-ray radiator and orientation information of a plurality of X-ray detectors,
select an X-ray detector of the plurality of X-ray detectors based on the orientation information of the X-ray radiator including the information indicating the X-ray radiation direction of the X-ray radiator and the orientation information of the plurality of X-ray detectors, and set a power mode of the selected X-ray detector to be a power consumption mode and a power mode of an unselected X-ray detector of the plurality of X-ray detectors to be a power save mode.

2. The X-ray apparatus of claim 1, wherein, when at least one X-ray detector of the plurality of X-ray detectors is coupled to a receptor, the controller is further configured to set a power mode of the receptor to be the same as a power mode of the at least one X-ray detector that is coupled to the receptor.

3. The X-ray apparatus of claim 1, wherein the controller is further configured to acquire the orientation information of the X-ray radiator based on a positioning mode of the X-ray apparatus, the positioning mode being one of a stand mode, a table mode, and a portable mode.

4. The X-ray apparatus of claim 1, wherein, when a non-usage time of the X-ray apparatus exceeds a threshold time, the controller is further configured to switch an operation mode of the X-ray apparatus to a sleep mode and to adaptively set the threshold time.

5. The X-ray apparatus of claim 4, wherein the controller is further configured to:
acquire a usage time distribution function that is a frequency of using the X-ray apparatus with respect to a time interval between scanning operations performed by the X-ray apparatus,
acquire a utility function based on the usage time distribution function, and
set a time to maximize the utility function as the threshold time.

6. The X-ray apparatus of claim 4, further comprising a collimator that comprises a blade configured to block the X-ray and a blade driver configured to move the blade,
wherein the controller is further configured to control the blade driver to move the blade to a first reference position and obtain a first relative position of the blade with respect to the first reference position until the operation mode is switched to the sleep mode.

7. The X-ray apparatus of claim 6, wherein, when the operation mode is switched to the sleep mode and then to a use mode, the controller is further configured to control the blade driver to move the blade to the first reference position and control the blade driver to move the blade by the first relative position from the first reference position.

8. The X-ray apparatus of claim 7, further comprising a plurality of filters configured to filter the X-ray and a filter driver configured to move the plurality of filters, wherein the controller is further configured to:
control the filter driver to move the plurality of filters to second reference positions and obtain second relative positions of the plurality of filters with respect to the second reference positions until the operation mode is switched to the sleep mode, and
when the operation mode is switched to the sleep mode and then to a use mode, control the filter driver to move the plurality of filters to the second reference positions and control the filter driver to move the plurality of filters by the second relative positions from the second reference positions.

9. The X-ray apparatus of claim 4, further comprising a mode indicator configured to indicate that the operation mode of the X-ray apparatus is the sleep mode.

10. The X-ray apparatus of claim 9, wherein:

the mode indicator comprises a light-emitting element, and
when the operation mode of the X-ray apparatus is the sleep mode, the light-emitting element is configured to flicker at a speed equal to or less than a predetermined speed.

11. A workstation comprising:
a communicator configured to receive orientation information of an X-ray radiator including information indicating an X-ray radiation direction of the X-ray radiator and orientation information of a plurality of X-ray detectors; and
a controller configured to:
select an X-ray detector of the plurality of X-ray detectors based on the orientation information of the X-ray radiator including the information indicating the X-ray radiation direction of the X-ray radiator and the orientation information of the plurality of X-ray detectors, and
set a power mode of the selected X-ray detector to be a power consumption mode and a power mode of an unselected X-ray detector of the plurality of X-ray detectors to be a power save mode.

12. The workstation of claim 11, wherein, when at least one X-ray detector of the plurality of X-ray detectors is coupled to a receptor, the controller is further configured to set a power mode of the receptor to be the same as a power mode of the at least one X-ray detector that is coupled to the receptor.

13. The workstation of claim 11, wherein the controller is further configured to acquire the orientation information of the X-ray radiator based on a positioning mode of the X-ray apparatus, the positioning mode being one of a stand mode, a table mode, and a portable mode.

14. The workstation of claim 11, wherein, when non-usage times of the X-ray apparatus and the workstation exceed a threshold time, the controller is further configured to switch an operation mode of the X-ray apparatus and the workstation to a sleep mode and to adaptively set the threshold time.

15. The workstation of claim 14, wherein the controller is further configured to:
acquire a usage time distribution function that is a frequency of using the X-ray apparatus with respect to a time interval between scanning operations performed by the X-ray apparatus,
acquire a utility function based on the usage time distribution function, and
set a time to maximize the utility function as the threshold time.

16. The workstation of claim 14, wherein the X-ray apparatus further comprises a collimator that comprises a blade configured to block an X-ray radiated from the X-ray radiator and a blade driver configured to move the blade, and
wherein the controller is further configured to control the blade driver to move the blade to a first reference position and obtain a first relative position of the blade with respect to the first reference position until the operation mode is switched to the sleep mode.

17. The workstation of claim 16, wherein, when the operation mode is switched to the sleep mode and then to a use mode, the controller is further configured to control the blade driver to move the blade to the first reference position and control the blade driver to move the blade by the first relative position from the first reference position.

18. The workstation of claim 17, wherein the X-ray apparatus further comprises a plurality of filters configured to filter the X-ray and a filter driver configured to move the plurality of filters, wherein the controller is further configured to:

control the filter driver to move the plurality of filters to second reference positions and obtain second relative positions of the plurality of filters with respect to the second reference positions until the operation mode is switched to the sleep mode, and when the operation mode is switched to the sleep mode and then to a use mode, control the filter driver to move the plurality of filters to the second reference positions and control the filter driver to move the plurality of filters by the second relative positions from the second reference positions.

19. A method of operating an X-ray system, the method comprising:

acquiring orientation information of an X-ray radiator including information indicating an X-ray radiation direction of the X-ray radiator and orientation information of at least one X-ray detector of a plurality of X-ray detectors;

selecting an X-ray detector of the plurality of X-ray detectors based on the orientation information of the X-ray radiator including the information indicating the X-ray radiation direction of the X-ray radiator and the orientation information of the at least one X-ray detector; and setting a power mode of the selected X-ray detector to be a power consumption mode and a power mode of an unselected X-ray detector of the plurality of X-ray detectors to be a power save mode.

20. A non-transitory computer readable storage medium having stored thereon a program, which when executed by a computer, performs the method defined in claim 19.

* * * * *